United States Patent [19]

Nohira et al.

[11] Patent Number: 5,686,020

[45] Date of Patent: Nov. 11, 1997

[54] MESOMORPHIC COMPOUND, LIQUID CRYSTAL COMPOSITION, LIQUID CRYSTAL DEVICE, DISPLAY APPARATUS AND DISPLAY METHOD

[75] Inventors: Hiroyuki Nohira, Urawa; Takao Takiguchi, Tokyo; Takashi Iwaki, Machida; Takeshi Togano, Yokohama; Yoko Yamada; Shinichi Nakamura, both of Atsugi; Koji Noguchi, Ageo, all of Japan

[73] Assignee: Canon Kabushiki Kaisha, Tokyo, Japan

[21] Appl. No.: 440,877

[22] Filed: May 15, 1995

Related U.S. Application Data

[63] Continuation of Ser. No. 755,041, Sep. 4, 1991, abandoned.

[30] Foreign Application Priority Data

Sep. 4, 1990 [JP] Japan ..................... 2-234990

[51] Int. Cl.⁶ ............ C09K 19/34; C09K 19/30; C09K 19/12; C07C 41/00
[52] U.S. Cl. .................. 252/299.61; 568/659; 568/660; 568/661
[58] Field of Search ............ 252/299.61, 299.66, 252/299.63, 299.6; 568/659, 660, 661

[56] References Cited

U.S. PATENT DOCUMENTS

| | | | |
|---|---|---|---|
| 4,367,924 | 1/1983 | Clark et al. | 350/334 |
| 4,865,763 | 9/1989 | Inoue et al. | 252/299.61 |
| 4,867,903 | 9/1989 | Nohira et al. | 252/299.61 |
| 4,892,675 | 1/1990 | Nohira et al. | 252/299.01 |
| 4,917,821 | 4/1990 | Mori et al. | 252/299.63 |
| 4,918,213 | 4/1990 | Nohira et al. | 558/271 |
| 5,073,306 | 12/1991 | Nohira et al. | 252/299.61 |
| 5,116,527 | 5/1992 | Coates et al. | 252/299.61 |
| 5,160,662 | 11/1992 | Satoh et al. | 252/299.61 |
| 5,290,478 | 3/1994 | Satoh et al. | 252/299.62 |
| 5,326,497 | 7/1994 | Buchecker et al. | 252/299.61 |

FOREIGN PATENT DOCUMENTS

| | | |
|---|---|---|
| 0313336 | 4/1989 | European Pat. Off. |
| 0316181 | 5/1989 | European Pat. Off. |
| 0335348 | 10/1989 | European Pat. Off. |
| 0385692 | 9/1990 | European Pat. Off. |
| 56-107216 | 8/1981 | Japan. |
| WO 11451 | 11/1989 | WIPO. |

OTHER PUBLICATIONS

Schadt, et al. "Voltage–Dependent Optical Activity of a Twisted Nematic Liquid Crystal," 18 *Applied Physics Letters*, No. 4, pp. 127–128 (Feb. 15, 1971).

*Primary Examiner*—C. H. Kelly
*Attorney, Agent, or Firm*—Fitzpatrick, Cella, Harper & Scinto

[57] ABSTRACT

A mesomorphic compound represented by the following formula (I):

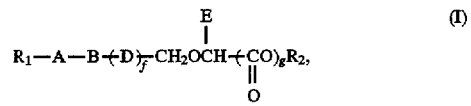

wherein $R_1$ denotes a linear or branched alkyl group having 1–18 carbon atoms capable of including one or non-neighboring two or more methylene groups which can be replaced with at least one species of

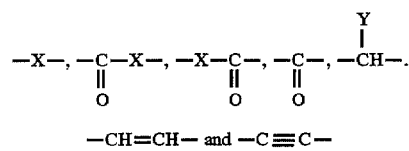

with the proviso that X denotes O or S and Y denotes halogen; $R_2$ denotes a linear or branched alkyl group having 1–18 carbon atoms; A, B and D independently denote

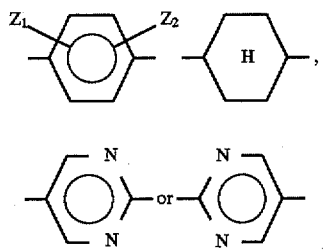

wherein $Z_1$ and $Z_2$ independently denote hydrogen, halogen, —$CH_3$, —CN or —$CF_3$; E denotes —$CH_3$, —$CH_2F$ or —$CF_3$; and f and g independently denote 0 or 1. The mesomorphic compound is effective for providing a ferroelectric liquid crystal composition showing an improved response speed and also effective for suppressing occurrence of reverse domain.

51 Claims, 4 Drawing Sheets

MESOMORPHIC COMPOUND, LIQUID CRYSTAL COMPOSITION, LIQUID CRYSTAL DEVICE, DISPLAY APPARATUS AND DISPLAY METHOD

This application is a continuation of application Ser. No. 07/755,041, filed Sep. 4, 1991, now abandoned.

FIELD OF THE INVENTION AND RELATED ART

The present invention relates to a novel mesomorphic compound, a liquid crystal composition a liquid crystal device, a display apparatus and a display method, and more particularly to a novel mesomorphic compound and a liquid crystal composition with improved responsiveness to an electric field, a liquid crystal device using the liquid crystal composition for use in a display device, a liquid crystal-optical shutter, etc., a display apparatus using the device, and a display method using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°–40° C., the response speed changes by a factor of about 20, so that it actually exceeds the range controllable by driving voltage and frequency.

Thus, as described hereinabove, commercialization of a ferroelectric liquid crystal device requires a liquid crystal composition assuming a chiral smectic phase which has not only a large spontaneous polarization but also a low viscosity, a high-speed responsiveness and a small temperature-dependence of response speed.

SUMMARY OF THE INVENTION

An object of the present invention is to provide a mesomorphic compound, a liquid crystal composition, particularly a chiral smectic liquid crystal composition, containing the mesomorphic compound for providing a practical ferroelectric liquid crystal device, a liquid crystal device using the liquid crystal composition and having a high response speed, a display apparatus using the device, and a display method using the composition and device.

According to the present invention, there is provided a mesomorphic compound represented by the following formula (I):

$$R_1-A-B+D)_f-CH_2OCH+CO)_gR_2, \quad \text{with E above CH, } \overset{\|}{O} \text{ below CO} \tag{I}$$

wherein $R_1$ denotes a linear or branched alkyl group having 1–18 carbon atoms capable of including one or non-neighboring two or more methylene groups which can be replaced with at least one species of $$-X-, \ -\underset{\underset{O}{\|}}{C}-X-, \ -X-\underset{\underset{O}{\|}}{C}-, \ -\underset{\underset{O}{\|}}{C}-, \ -\underset{\underset{Y}{|}}{CH}-.$$

$$-CH=CH- \text{ and } -C\equiv C-$$

with the proviso that X denotes O or S and Y denotes halogen; $R_2$ denotes a linear or branched alkyl group having 1–18 carbon atoms; A, B and D independently denote

[benzene ring with Z₁ and Z₂ substituents], [cyclohexane ring with H],

[pyrimidine ring] or [pyrazine ring]

wherein $Z_1$ and $Z_2$ independently denote hydrogen, halogen, $-CH_3$, $-CN$ or $-CF_3$; E denotes $-CH_3$, $-CH_2F$ or $-CF_3$; and f and g independently denote 0 or 1.

According to the present invention, there is further provided a liquid crystal composition containing at least one species of the mesomorphic compound as described above.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method using the liquid crystal composition or the liquid crystal device described above and switching the alignment direction of liquid crystal molecules by applying voltages to the liquid crystal composition to effect display.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
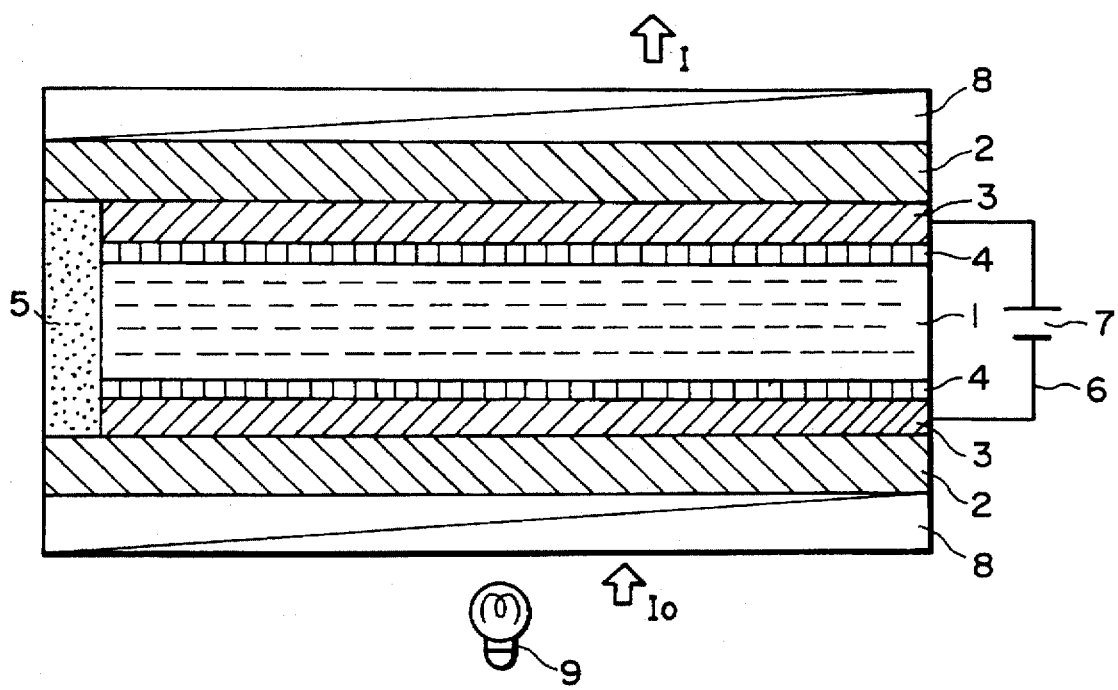
FIG. 1 is a schematic sectional view of a liquid crystal display device using a liquid crystal composition assuming a chiral smectic phase.

In the formula (I) as described above, preferred examples of $R_1$ may include a linear or branched alkyl group having 14 18 carbon atoms capable of including one or two or more non-neighboring methylene groups which can be replaced with at least one species of $$-X-, \ -\underset{\underset{O}{\|}}{C}-, \ \text{and} \ -\underset{\underset{Y}{|}}{CH}-.$$

Further, $R_1$ may preferably include the following groups (i) to (iv):

(i) $-G-C_aH_{2a+1}$-n wherein G denotes a single bond, $$-O-, \ -S- \ \text{or} \ -\underset{\underset{O}{\|}}{C}-;$$

and a is an integer of 1–18, particularly 3–14;

(ii)

$$-G+CH_2)_m\overset{CH_3}{\underset{|}{C}}HC_nH_{2n+1}$$

wherein G denotes a single bond $$-O-, \ -S- \ \text{or} \ -\underset{\underset{O}{\|}}{C}-;$$

m is an integer of 0–7 and n is an integer of 1–9 (optically active or inactive);

(iii)

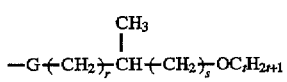

wherein G denotes a single bond,

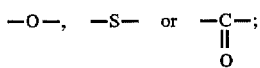

r is an integer of 0–7; s is 0 or 1 and t is an integer of 1–14 (optically active or inactive); and (iv)

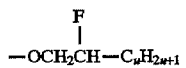

wherein u is an integer of 1–16 (optically active or inactive).

Preferred examples of $R_2$ may include an n-alkyl group having 4–8 carbon atoms when E denotes —$CF_3$ or —$CH_2F$; an n-alkyl group having 2–12 carbon atoms when E denotes —$CH_3$ and g is 0; and an n-alkyl group having 1–12 carbon atoms when E denotes —$CH_3$ and g is 1.

Further, at least two constituents at A, B and D may preferably be

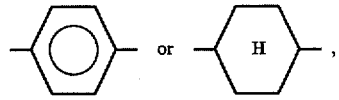

respectively.

The mesomorphic compound of the present invention may include a racemic mixture and an optically active compound, preferably an optically active compound.

The mesomorphic compounds represented by the formula (I) may be synthesized through the following reaction scheme.

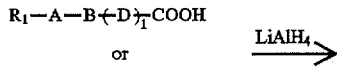
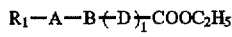
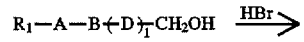
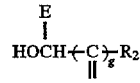
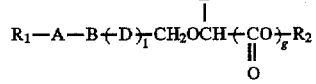

In the above, $R_1$, $R_2$, A, B, D, E, f and g respectively the same as defined in the above formula (I).

Specific examples of the mesomorphic compounds represented by the formula (I) may include those shown in the following structural formulas.

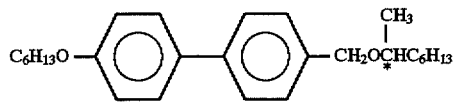    (1)

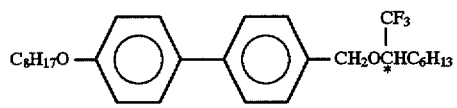    (2)

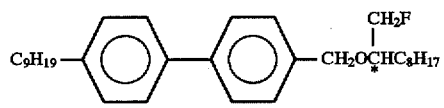    (3)

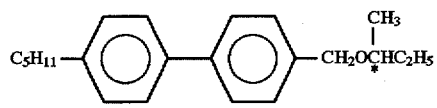    (4)

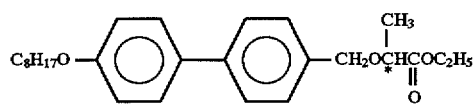    (5)

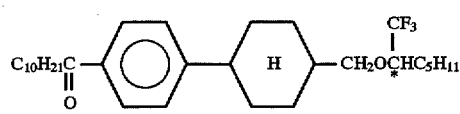    (6)

-continued $$C_8H_{17}O-\phenyl-H-CH_2O\overset{*}{C}H(CF_3)C_4H_9 \quad (7)$$

$$C_{13}H_{27}O-\phenyl-H-CH_2O\overset{*}{C}H(CH_3)C_4H_9 \quad (8)$$

$$C_6H_{13}\overset{*}{C}H(CF_3)OCH_2-\phenyl-H-C_5H_{11} \quad (9)$$

$$C_3H_7OC(=O)\overset{*}{C}H(CH_3)OCH_2-\phenyl-H-C_8H_{17} \quad (10)$$

$$C_{11}H_{23}O-\phenyl-pyrazine-CH_2O\overset{*}{C}H(CF_3)C_8H_{17} \quad (11)$$

$$C_{12}H_{25}-\phenyl-pyrazine-CH_2O\overset{*}{C}H(CH_3)C_8H_{17} \quad (12)$$

$$C_6H_{13}\overset{*}{C}H(CH_2F)OCH_2-\phenyl-pyrazine-C_8H_{16}-CH=CH_2 \quad (13)$$

$$C_5H_{11}\overset{*}{C}H(CF_3)OCH_2-\phenyl-pyrazine-C_{13}H_{27} \quad (14)$$

$$C_7H_{15}\overset{*}{C}H(CH_3)OCH_2-\phenyl-pyrimidine-C_3H_7 \quad (15)$$

$$C_5H_{11}OC(=O)\overset{*}{C}H(CH_3)OCH_2-\phenyl-pyrimidine-C_5H_{11} \quad (16)$$

$$C_7H_{15}\overset{*}{C}H(CF_3)OCH_2-\phenyl-pyrimidine-C_8H_{17} \quad (17)$$

$$C_6H_{13}\overset{*}{C}H(CH_2F)OCH_2-\phenyl-pyrimidine-C_{10}H_{21} \quad (18)$$

$$C_6H_{13}\overset{*}{C}H(CF_3)OCH_2-\phenyl-pyrimidine-C_{10}H_{21} \quad (19)$$

$$C_6H_{13}\overset{*}{C}H(CH_3)OCH_2-\phenyl-pyrimidine-C_{10}H_{21} \quad (20)$$

-continued
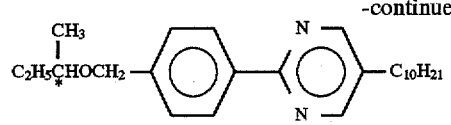 (21)
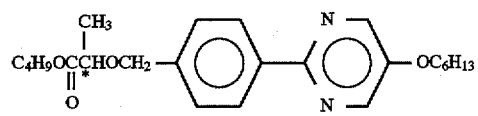 (22)
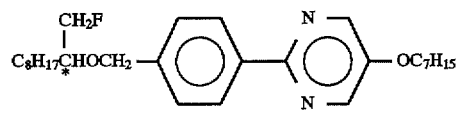 (23)
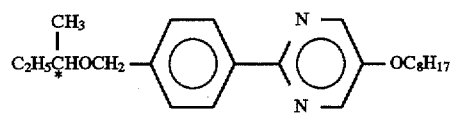 (24)
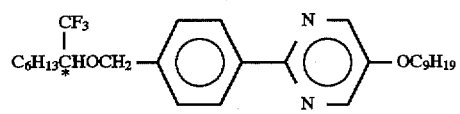 (25)
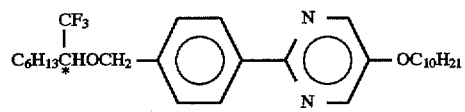 (26)
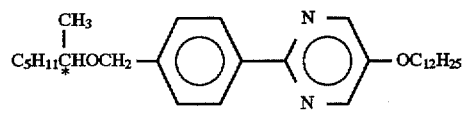 (27)
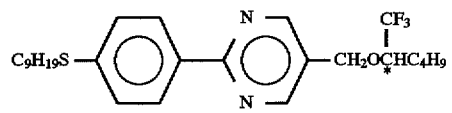 (28)
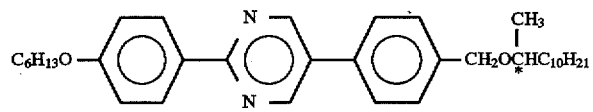 (29)
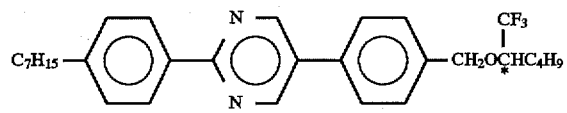 (30)
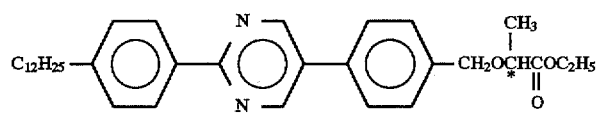 (31)
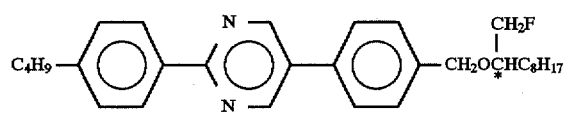 (32)
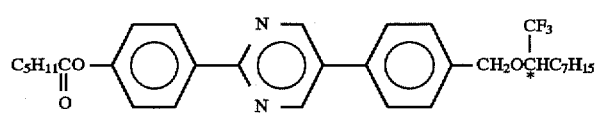 (33)
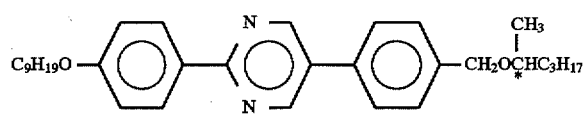 (34)

-continued
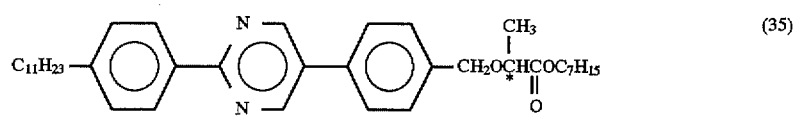 (35)
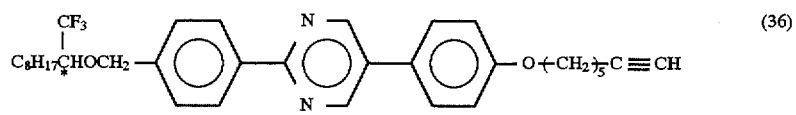 (36)
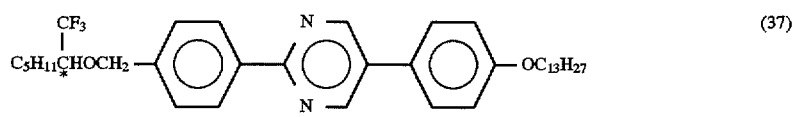 (37)
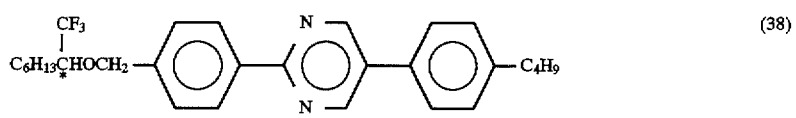 (38)
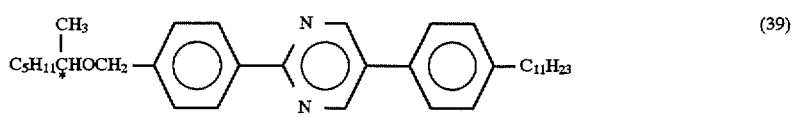 (39)
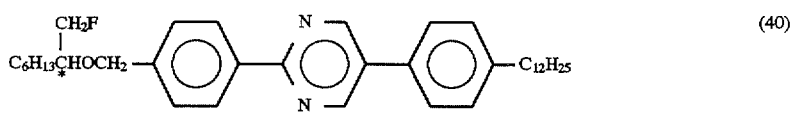 (40)
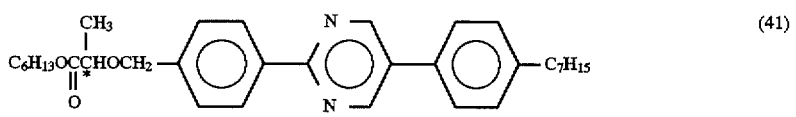 (41)
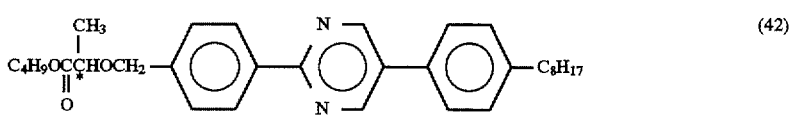 (42)
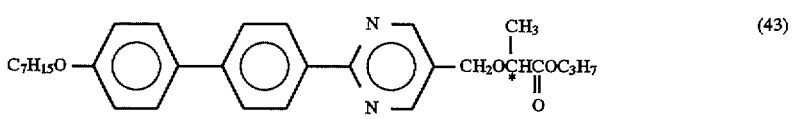 (43)
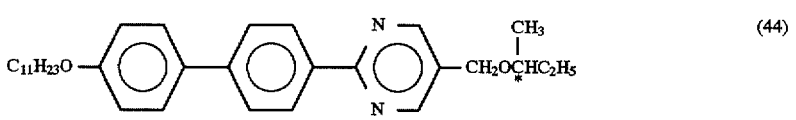 (44)
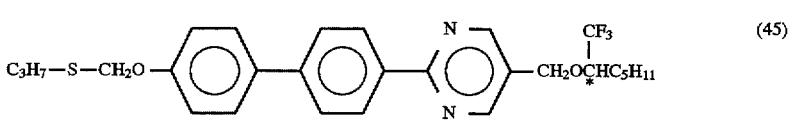 (45)
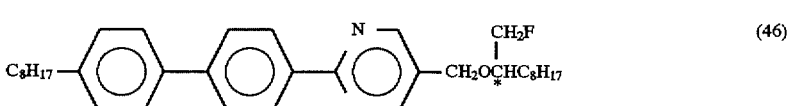 (46)
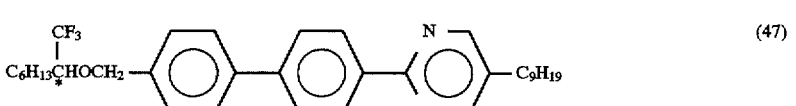 (47)

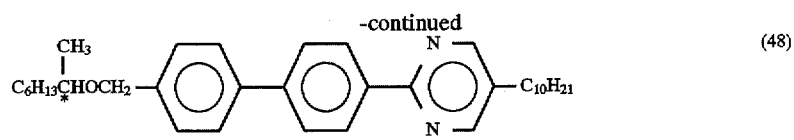 (48)
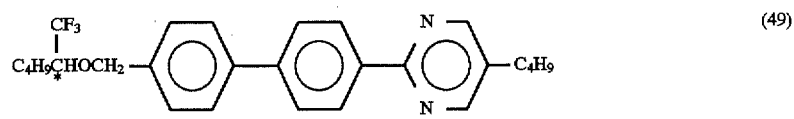 (49)
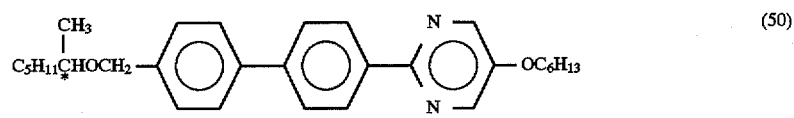 (50)
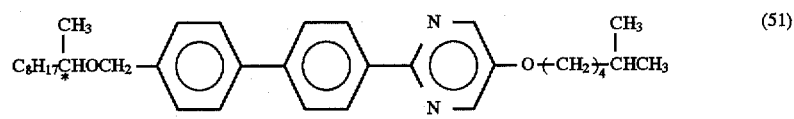 (51)
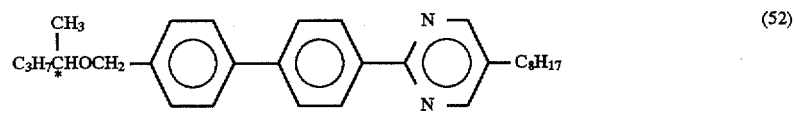 (52)
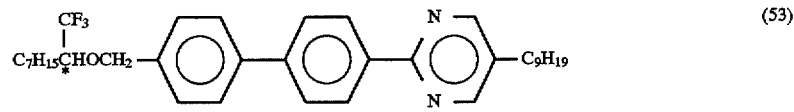 (53)
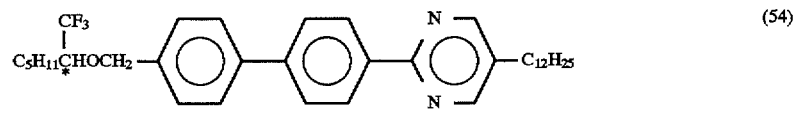 (54)
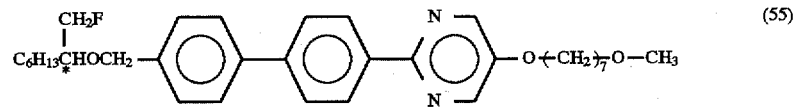 (55)
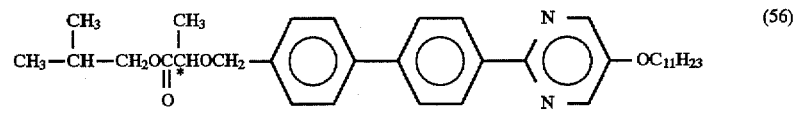 (56)
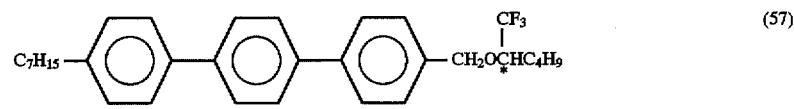 (57)
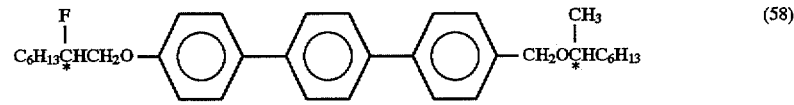 (58)
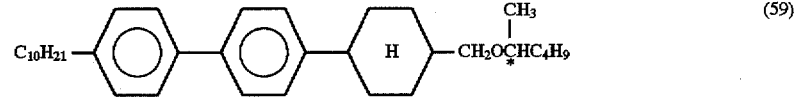 (59)
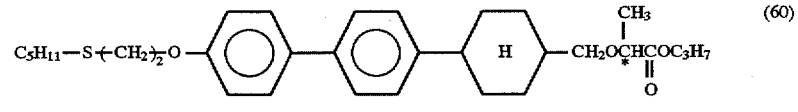 (60)
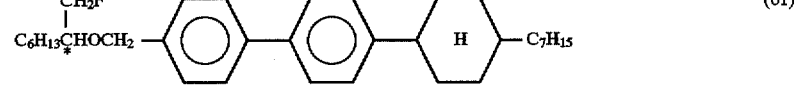 (61)

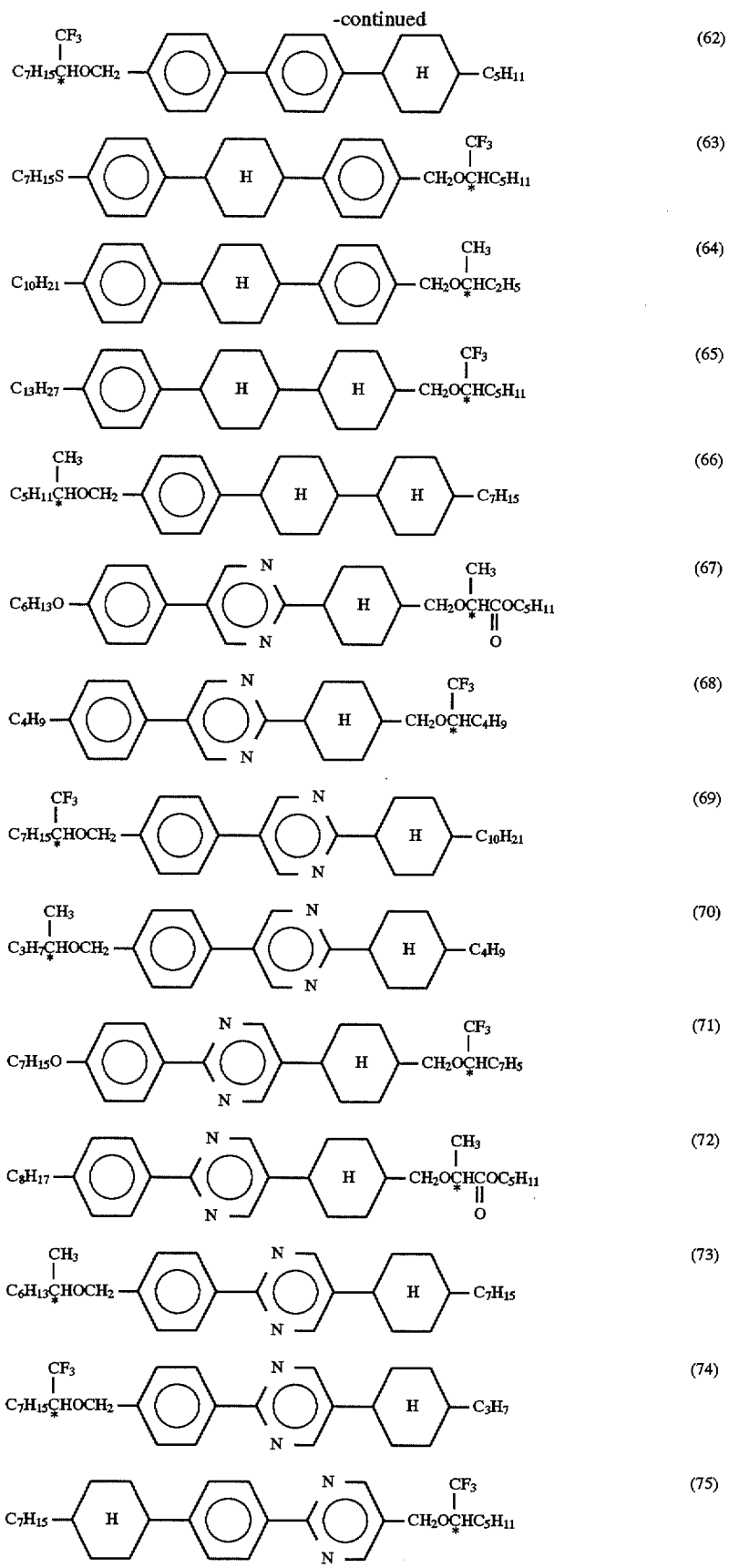

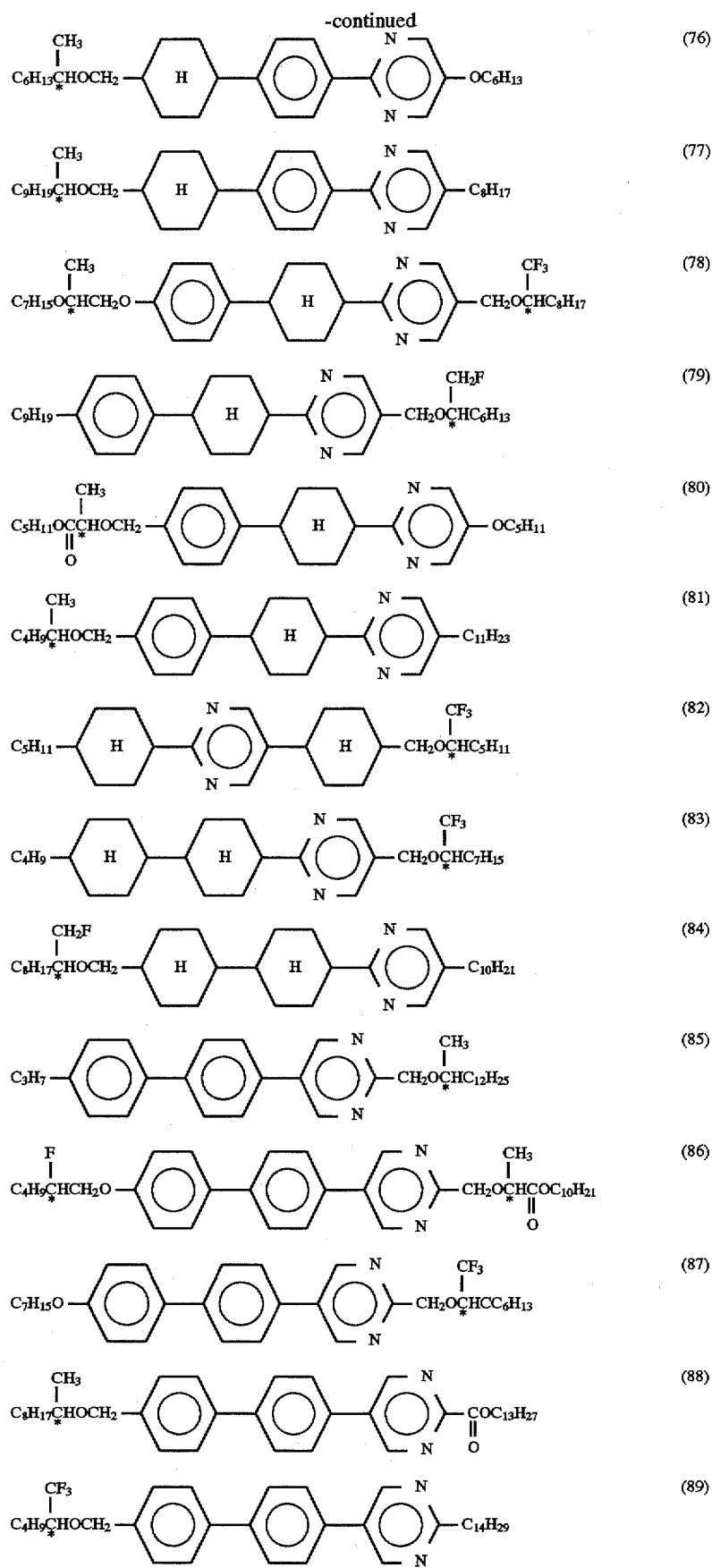

-continued
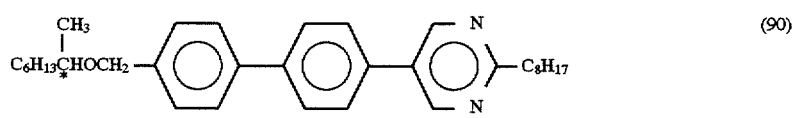 (90)
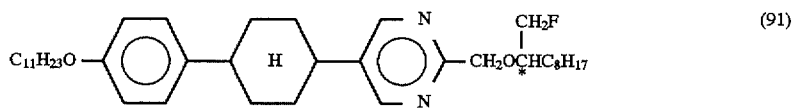 (91)
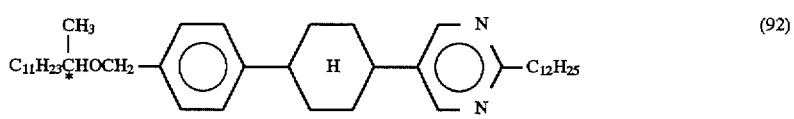 (92)
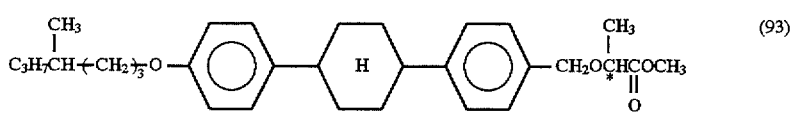 (93)
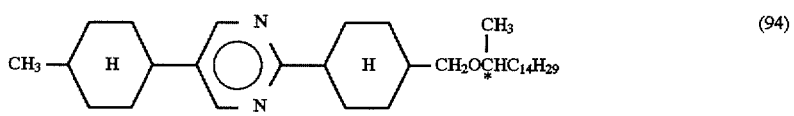 (94)
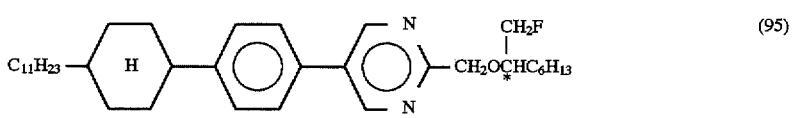 (95)
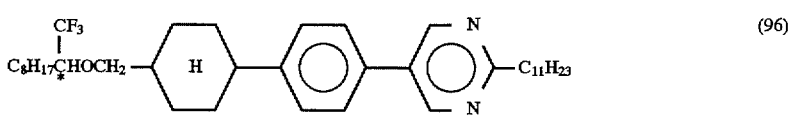 (96)
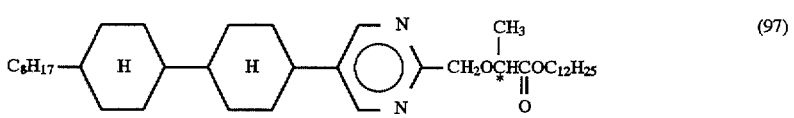 (97)
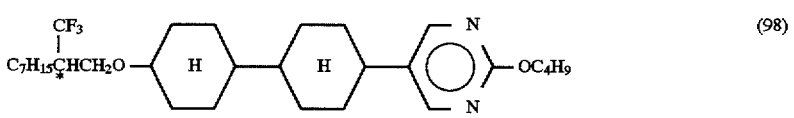 (98)
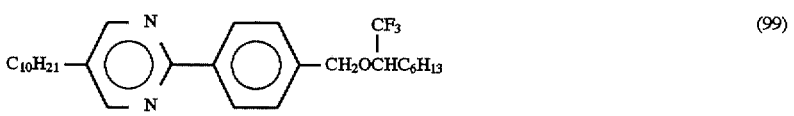 (99)
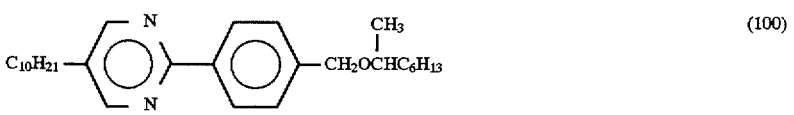 (100)
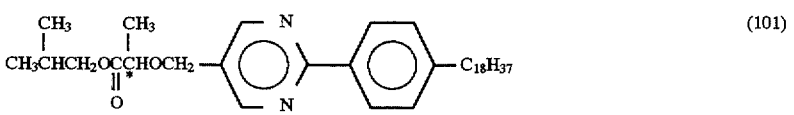 (101)
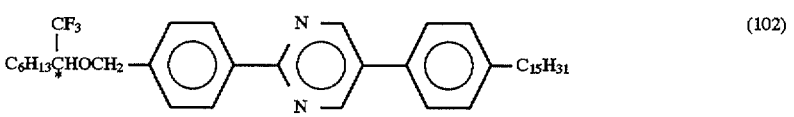 (102)

-continued
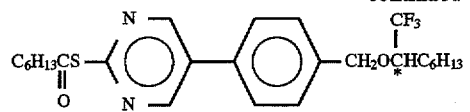 (103)
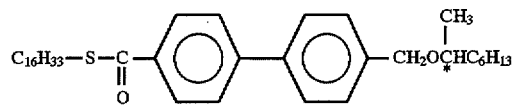 (104)
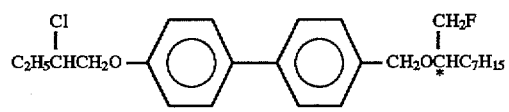 (105)
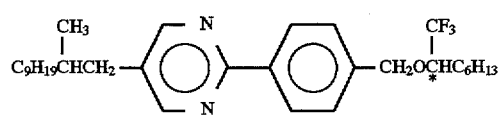 (106)
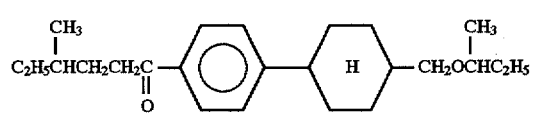 (107)
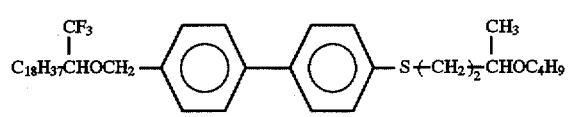 (108)
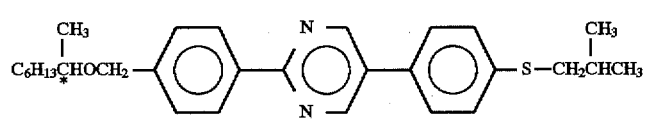 (109)
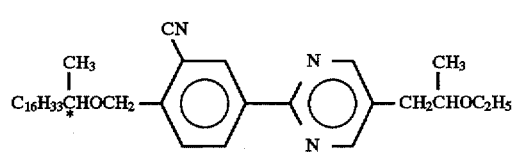 (110)
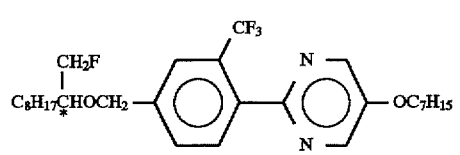 (111)
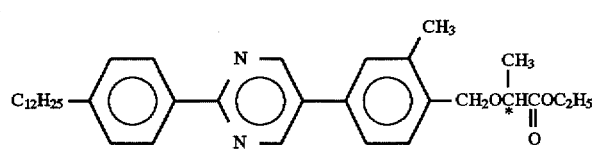 (112)
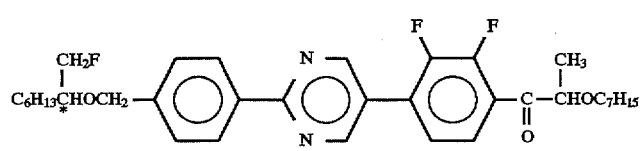 (113)
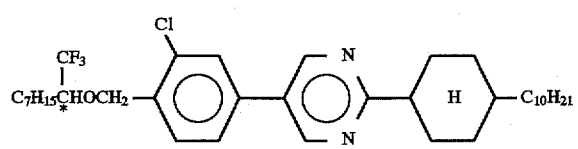 (114)

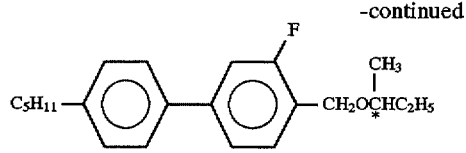

(115)

The liquid crystal composition according to the present invention may be obtained by mixing at least one species of the compound represented by the formula (I) and another mesomorphic compound in appropriate proportions. The liquid crystal composition according to the present invention may preferably be formulated as a liquid crystal composition capable of utilizing ferroelectricity, particularly a liquid crystal composition showing a chiral smectic phase.

Specific examples of another mesomorphic compound as described above may include those denoted by the following formulas (III) to (XII).

respectively denote a single bond,

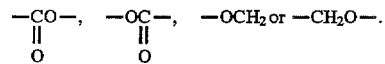

In the formula (III), preferred compounds thereof may include those represented by the following formulas (IIIa) to (IIId):

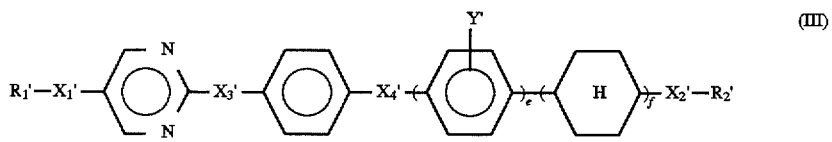
(III)

wherein e denotes 0 or 1 and f denotes 0 or 1 with proviso that e+f=0 or 1; Y' denotes H, halogen, $CH_3$ or $CF_3$; $X_1'$ and $X_2'$ respectively denote a single bond,

(IIIa)

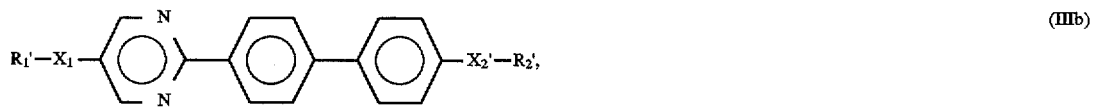
(IIIb)

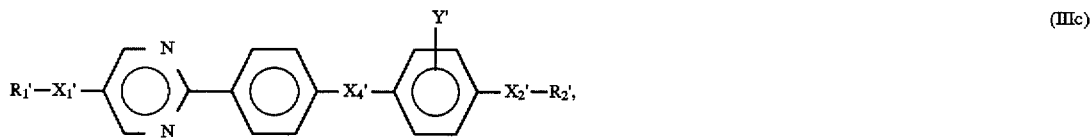
(IIIc)

and

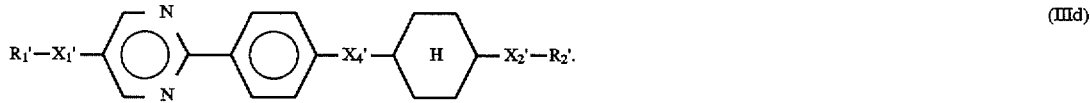
(IIId)

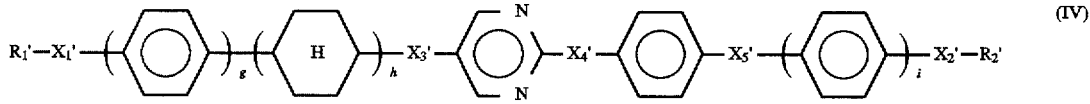
(IV)

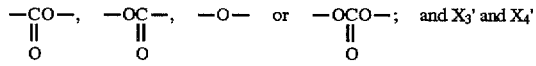

wherein g and h respectively denote 0 or 1 with proviso that g+h=1; i denotes 0 or 1; $X_1'$ and $X_2'$ respectively denote a single bond,

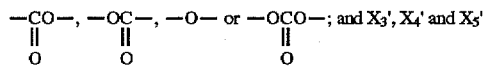

respectively denote a single bond,

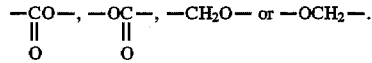

In the formula (IV), preferred compounds thereof may include those represented by the following formulas (IVa) to (IVc):

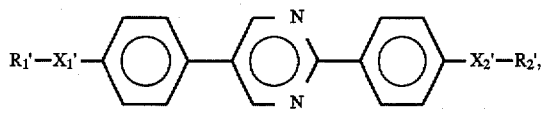
(IVa)

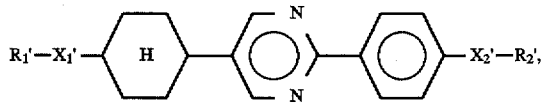
(IVb)

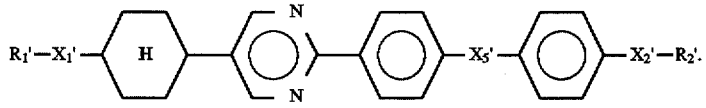
(IVc)

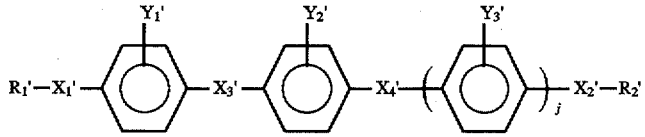
(V)

wherein j denotes 0 or 1; $Y_1'$, $Y_2'$ and $Y_3'$ respectively denote H, halogen, $CH_3$ or $CF_3$; $X_1'$ and $X_2'$ respectively denote a single bond, —CO—, —OC—, —O— and —OCO—;
  ‖           ‖                      ‖
  O          O                      O and $X_3'$ and $X_4'$ respectively denote a single bond, —CO—, —OC—, —CH$_2$O—, —OCH$_2$—, CH$_2$CH$_2$—, —CS—,
  ‖           ‖                                                       ‖
  O          O                                                       O -continued —SC—, (CH$_2$)$_2$CS—, (CH$_2$)CO—, —CH=CH—CO— or —O—.
  ‖              ‖                    ‖                              ‖
  O             O                   O                              O In the formula (V), preferred compounds thereof may include those represented by the following formulas (Va) and (Vb):

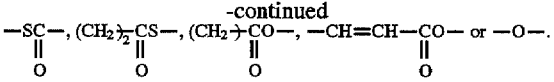
(Va)

and

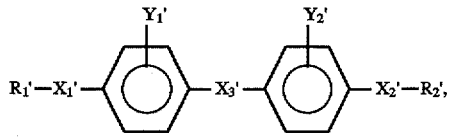
(Vb)

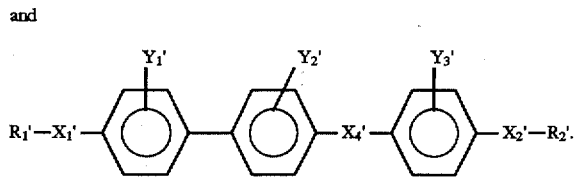

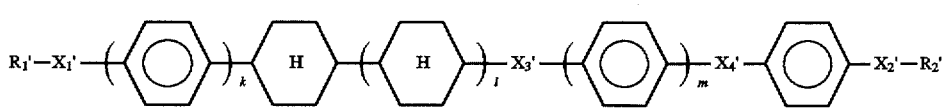
(VI)

wherein k, l and m respectively denote 0 or 1 with proviso that k+l+m=0, 1 or 2; $X_1'$ and $X_2'$ respectively denote a single bond,

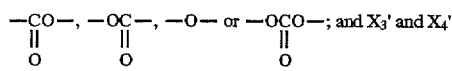

respectively denote a single bond,

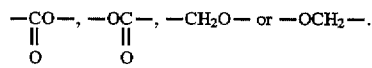

In the formula (VI), preferred compounds thereof may include those represented by the following formulas (VIa) to (VIf):

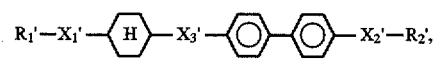 (VIa)

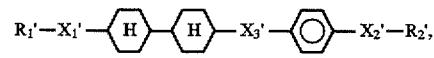 (VIb)

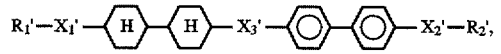 (VIc)

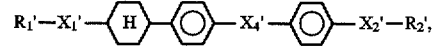 (VId)

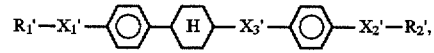 (VIe)

and

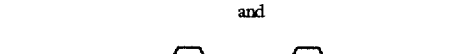 (VIf)

Herein, $R_1'$ and $R_2'$ respectively denote a linear or branched alkyl group having 1–18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of

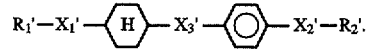

with proviso that $R_1'$ and $R_2'$ respectively do not connect to a ring structure by a single bond when $R_1'$ and $R_2'$ respectively denote a halogenated alkyl group containing one methylene group replaced with —CH halogen- or —CH ($CF_3$)—.

Further, preferred examples of $R_1'$ and $R_2'$ may respectively include those represented by the following groups (i) to (ix):

i) a linear alkyl group having 1–15 carbon atoms;

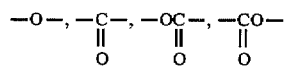

wherein p denotes an integer of 0–5 and q denotes an integer of 2–11 (optically active or inactive);

wherein r denotes an integer of 0–6, s denotes 0 or 1, and t denotes an integer of 1–14 (optically active or inactive);

iv) $(CH_2)_u\overset{*}{C}H(F)—C_vH_{2v+1}$ wherein u denotes 0 or 1 and v denotes an integer of 1–16;

v) $—CHCH_3COC_wH_{2w+1}$ (with C=O)

wherein w denotes an integer of 1–15 (optically active or inactive);

vi) $\mathrm{+CH_2)_x\overset{*}{C}H(CF_3)—C_yH_{2y+1}}$ wherein x denotes an integer of 0–2 and y denotes an integer of 1–5.

vii) $—\overset{*}{C}H(CF_3)CH_2COC_zH_{2z+1}$ (with C=O)

wherein z denotes an integer of 1–15.

viii) $\mathrm{+CH_2)_A\overset{*}{C}H(CN)—C_BH_{2B+1}}$ wherein A denotes an integer of 0–2 and B denotes an integer of 1–15 (optically active or inactive); and xi) $\mathrm{+CH_2)_C\overset{*}{C}(CH)(CH_3)—C_DH_{2D+1}}$ wherein C denotes an integer of 0–2 and D denotes an integer of 1–15 (optically active or inactive).

In the above-mentioned formula (III), more preferred compounds thereof may include those represented by the formulas (IIIaa) to (IIIdc):

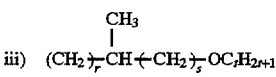 (IIIaa)

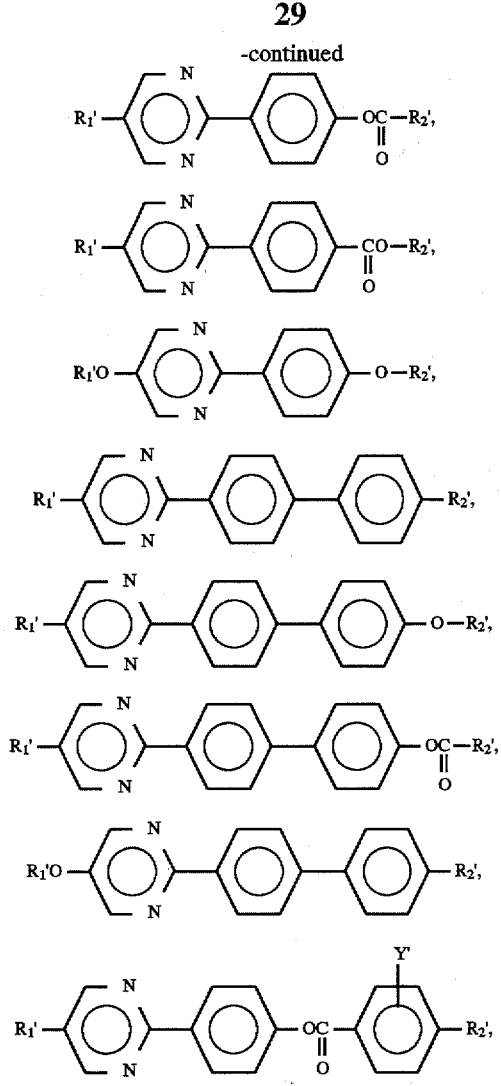
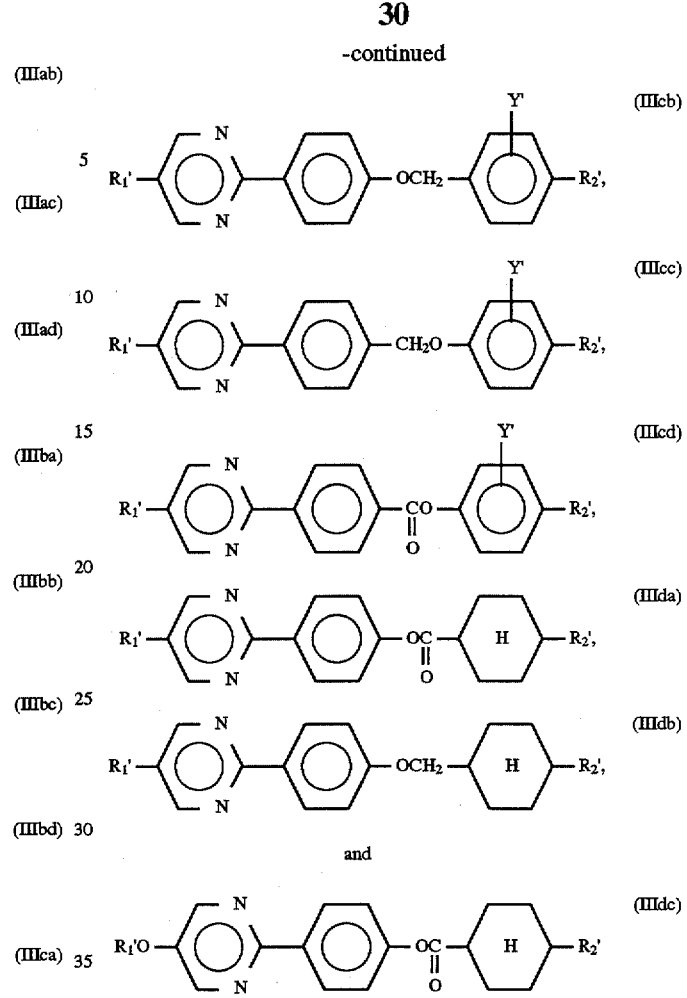
In the above-mentioned formula (IV), more preferred compounds thereof may include those represented by the formulas (IVaa) to (IVcd):
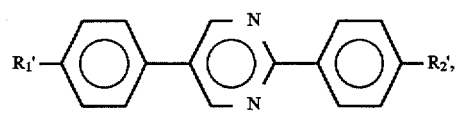
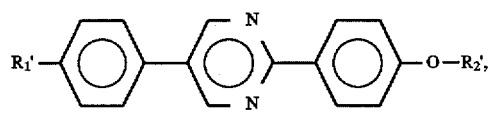
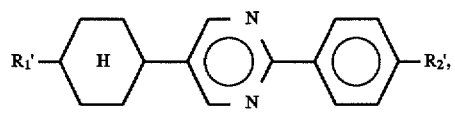
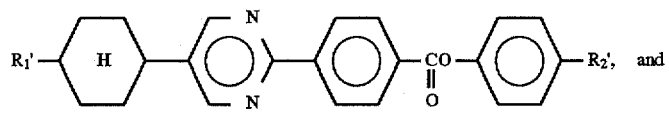
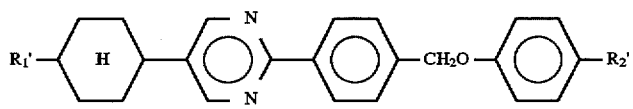

In the above-mentioned formula (V), more preferred compounds thereof may include those represented by the formulas (Vaa) to (Vbf):

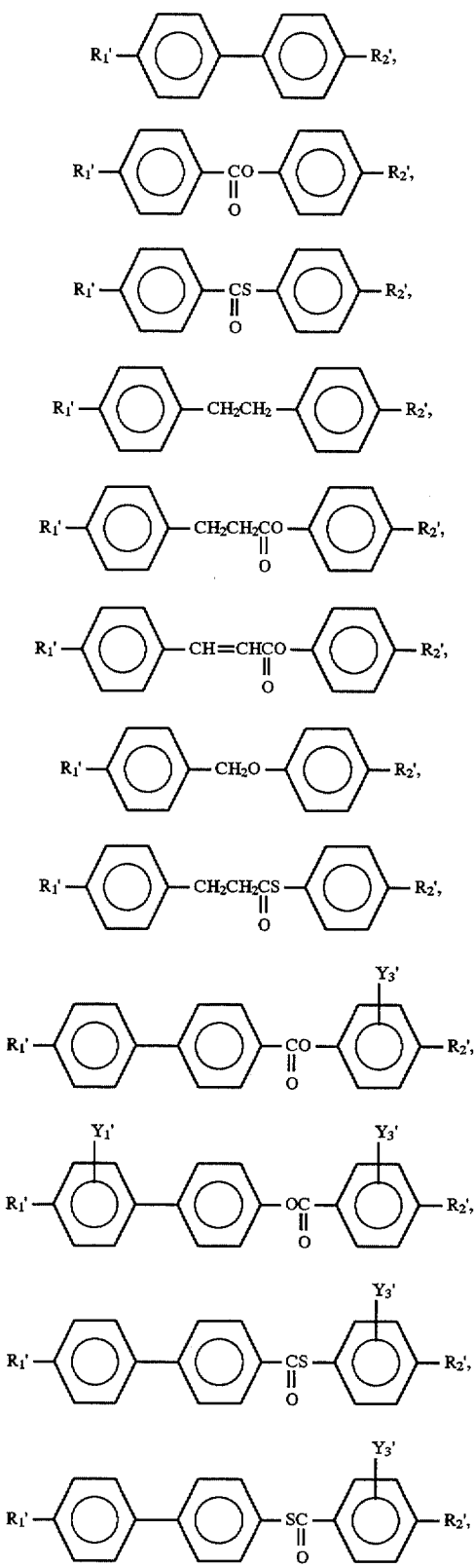

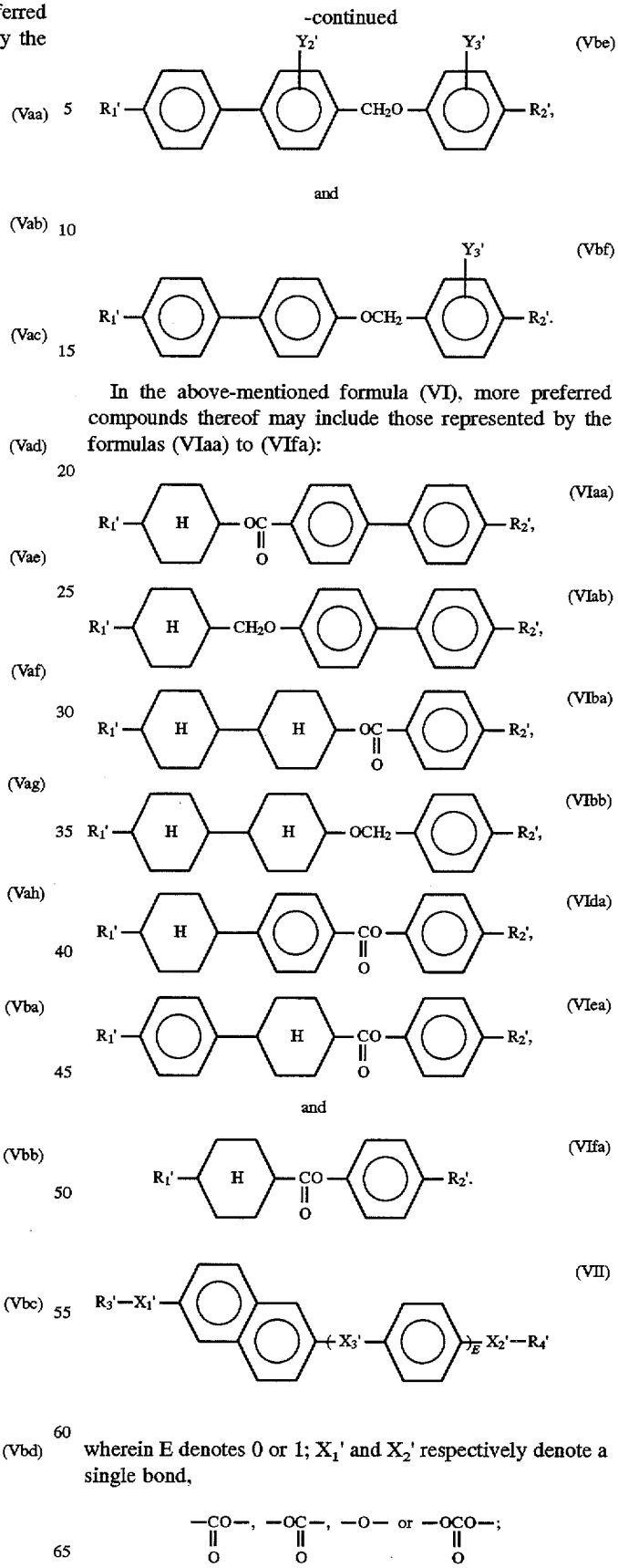

In the above-mentioned formula (VI), more preferred compounds thereof may include those represented by the formulas (VIaa) to (VIfa):

wherein E denotes 0 or 1; $X_1'$ and $X_2'$ respectively denote a single bond, $$-\underset{\underset{O}{\|}}{C}O-,\ -O\underset{\underset{O}{\|}}{C}-,\ -O-\ \text{or}\ -O\underset{\underset{O}{\|}}{C}O-;$$

and $X_3'$ denotes a single bond,

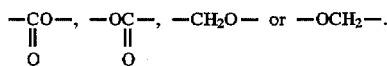

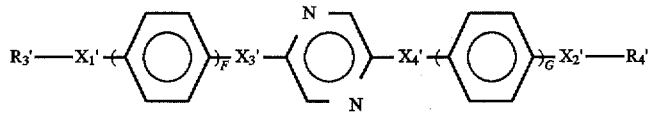

(VII)

wherein F and G respectively denote 0 or 1; $X_1'$ and $X_2'$ respectively denote a single bond,

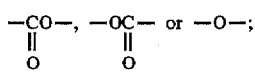

and $X_3'$ and $X_4'$ respectively denote a single bond,

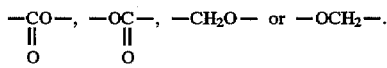

In the above formula (VII), preferred compounds thereof may include those represented by the following formulas (VIIa) and (VIIb):

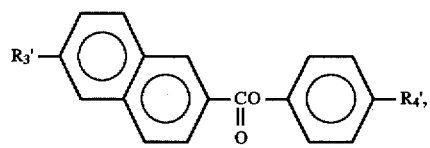

(VIIa)

and

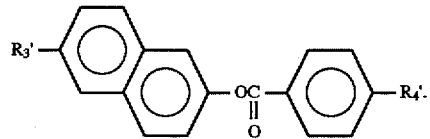

(VIIb)

In the above formula (VIII), preferred compounds thereof may include those represented by the following formulas (VIIIa) and (VIIIb).

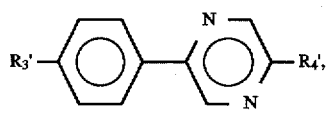

(VIIIa)

and

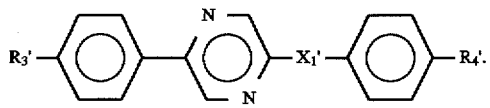

(VIIIb)

More preferred compounds of the formula (VIII) may include those represented by the formulas (VIIIaa) to (VIIIbb):

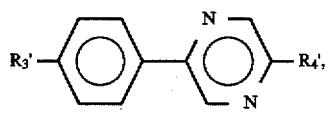

(VIIIaa)

(VIII)

-continued

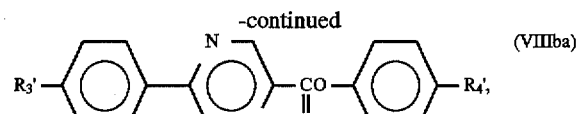

(VIIIba)

and

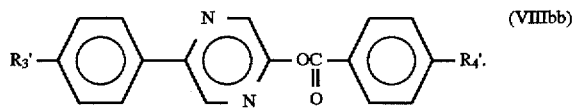

(VIIIbb)

Herein, $R_3'$ and $R_4'$ respectively denote a linear or branched alkyl group having 1–18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of

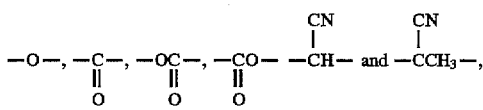

with proviso that $R_3'$ and $R_4'$ respectively do not connect to a ring structure by a single bond when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) a linear alkyl group having 1–15 carbon atoms;

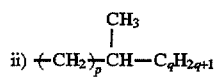

wherein p denotes an integer of 0–5 and q denotes an integer of 2–11 (optically active or inactive);

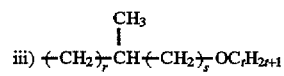

wherein r denotes an integer of 0–6, s denotes 0 or 1, and t denotes an integer of 1–14 (optically active or inactive);

iv) 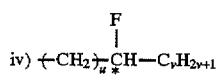

wherein u denotes an integer of 0 or 1 and v denotes an integer of 1–16;

v) 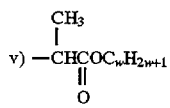

wherein w denotes an integer of 1–15 (optically active or inactive);

vi) 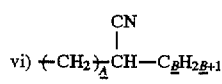

wherein A denotes an integer of 0–2 and B denotes an integer of 1–15 (optically active or inactive); and vii) 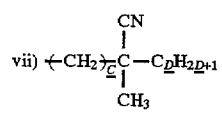

wherein C denotes an integer of 0–2 and D denotes an integer of 1–15 (optically active or inactive).

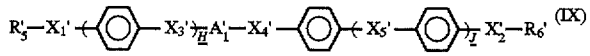

wherein H and J respectively denote 0 or 1 with proviso that H+J=0 or 1; $X_1'$ and $X_2'$ respectively denote a single bond,

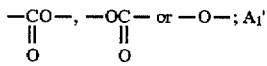

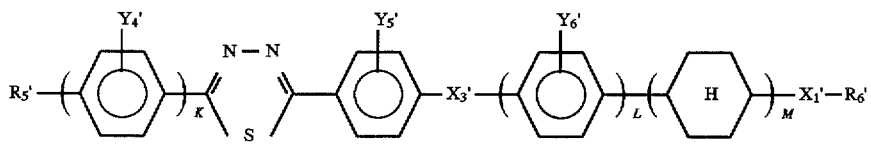

denotes

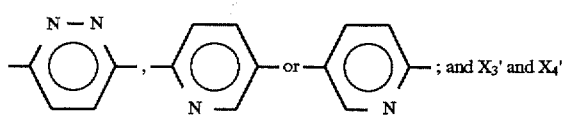 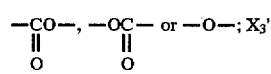

respectively denote a single bond,

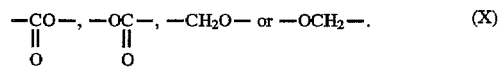 (X)

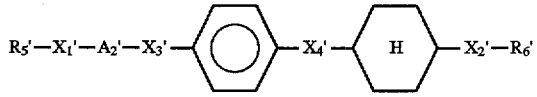

wherein $X_1'$ and $X_2'$ respectively denote a single bond,

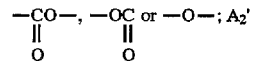

denotes

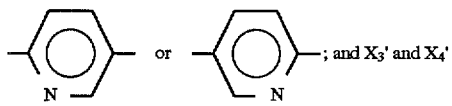

respectively denote a single bond,

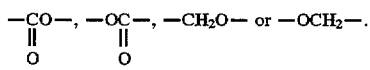

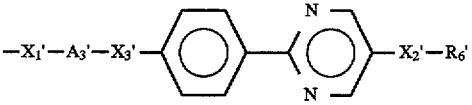 (XI)

wherein $X_1'$ and $X_2'$ respectively denote a single bond,

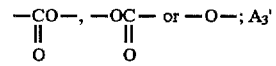

denotes

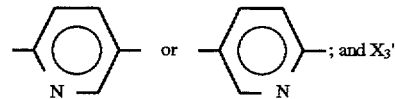

respectively denotes a single bond,

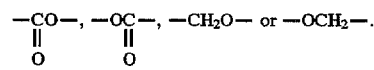

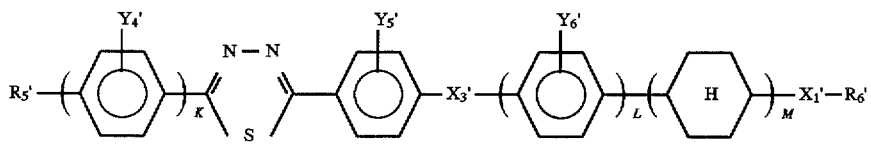 (XII)

wherein K, L and M respectively denote 0 or 1 with the proviso that K+L+M=0 or 1; $X_1'$ denotes a single bond,

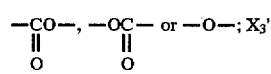

denotes a single bond,

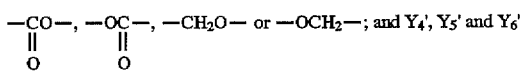

respectively denote H or F.

In the above formula (IX), preferred compounds thereof may include those represented by the following formulas (IXa) to (IXc):

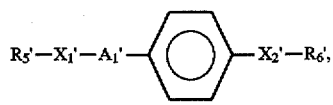 (IXa)

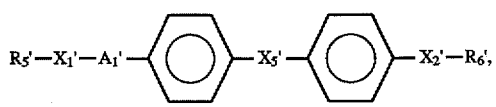 (IXb)

and

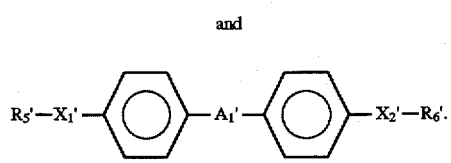 (IXc)

In the above formula (X), preferred compounds thereof may include those represented by the following formulas (Xa) and (Xb):

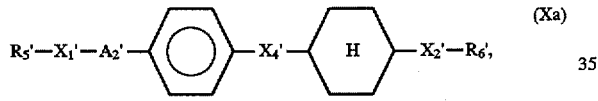 (Xa)

and

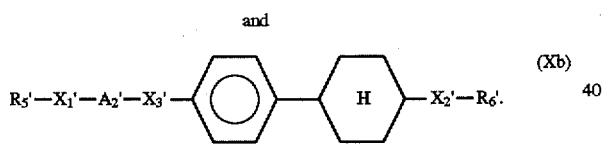 (Xb)

In the above formula (XII), preferred compounds thereof may include those represented by the following formulas (XIIa) and (XIId):

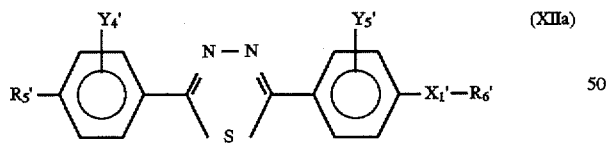 (XIIa)

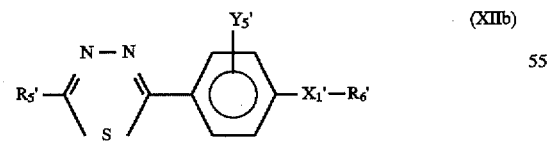 (XIIb)

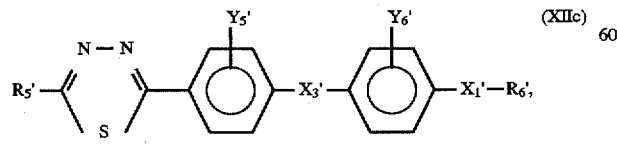 (XIIc)

and

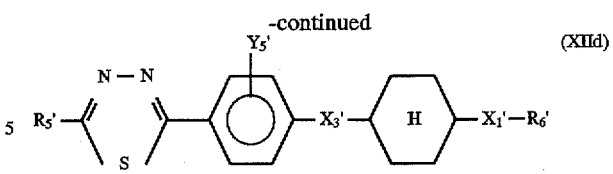 (XIId)

In the above-mentioned formula (IX), preferred compounds thereof may include those represented by the formulas (IXaa) to (IXcc):

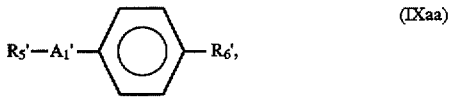 (IXaa)

 (IXab)

 (IXac)

 (IXad)

 (IXba)

 (IXbb)

 (IXbc)

 (IXbd)

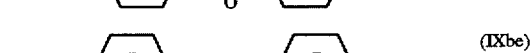 (IXbe)

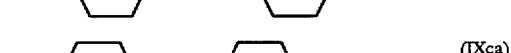 (IXca)

 (IXcb)

and

 (IXcc)

In the above-mentioned formula (X), more preferred compounds thereof may include those represented by the formulas (Xaa) to (Xbb):

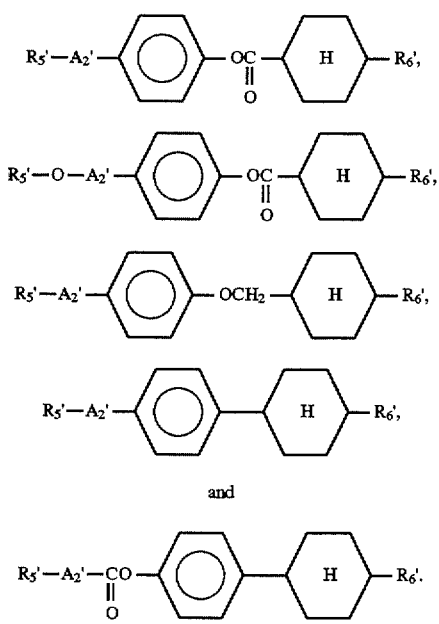

In the above formula (XI), preferred compounds thereof may include those represented by the following formulas (XIa) to (XIg):

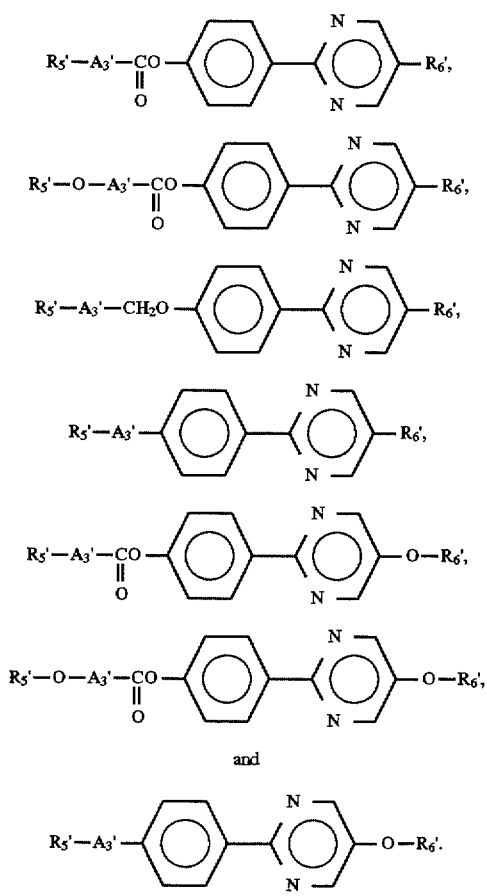

In the above-mentioned formula (XII), more preferred compounds thereof may include those represented by the formula (XIIaa) to (XIIdb):

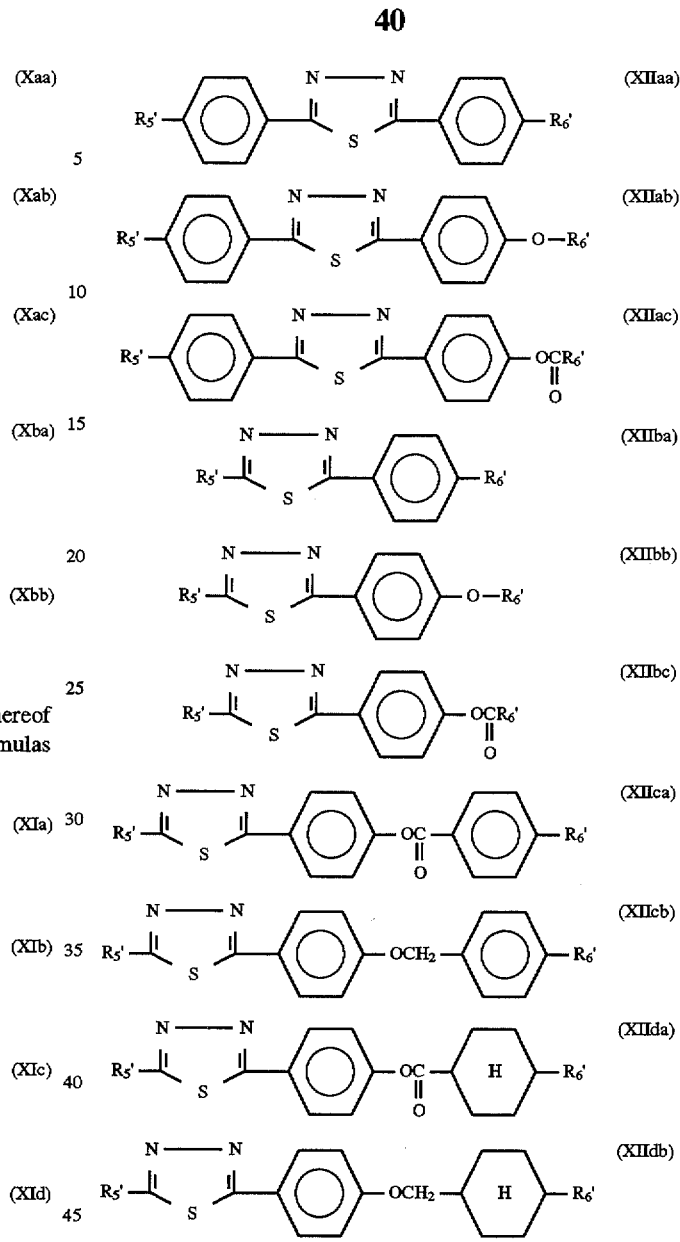

Herein, $R_5'$ and $R_6'$ respectively denote a linear or branched alkyl group having 1–18 carbon atoms capable of including one non-neighboring two or more methylene groups other than those directly connected to $X_1'$ or $X_2'$ which can be replaced with at least one species of

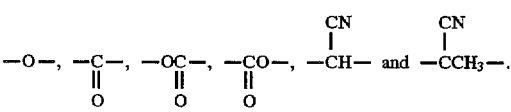

Further, preferred examples of $R_5'$ and $R_6'$ may respectively include those represented by the following groups (i) to (vi):

i) a linear alkyl group having 1–15 carbon atoms;

ii) 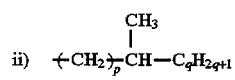

wherein p denotes an integer of 0–5 and q denotes an integer of 2–11 (optically active or inactive);

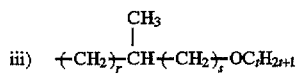

wherein r denotes an integer of 0–6, s denotes 0 or 1, and t denotes an integer of 1–14 (optically active or inactive);

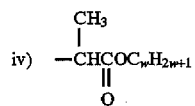

wherein w denotes an integer of 1–15 (optically active or inactive);

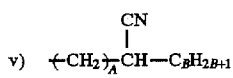

wherein A denotes an integer of 0–2 and B denotes an integer of 1–15 (optically active or inactive); and

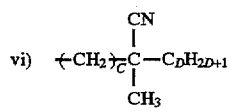

wherein C denotes an integer of 0–2 and D denotes an integer of 1–15 (optically active or inactive).

In formulating the liquid crystal composition according to the present invention, the liquid crystal composition may desirably contain 1–80 wt. %, preferably 1–60 wt. %, more preferably 1–40 wt. % of a mesomorphic compound represented by the formula (I).

Further, when two or more species of the compounds represented by the formula (I) are used, the liquid crystal composition may desirably contain 1–80 wt. %, preferably 1–60 wt. %, more preferably 1–40 wt. %, of the two or more species of the compounds represented by the formula (I).

The liquid crystal device according to the present invention may preferably be prepared by heating the liquid crystal composition assuming a chiral smectic phase prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The ferroelectric liquid crystal provided by the composition of the present invention may desirably comprise a SmC* phase (chiral smectic C phase) in a wide temperature range including room temperature (particularly, broad in a lower temperature side) and also shows high-speed responsiveness, a smaller temperature-dependence of response speed and wide drive voltage margin when contained in a device.

Particularly, in order to show a good alignment characteristic to form a uniform monodomain, the ferroelectric liquid crystal may show a phase transition series comprising isotropic phase—Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
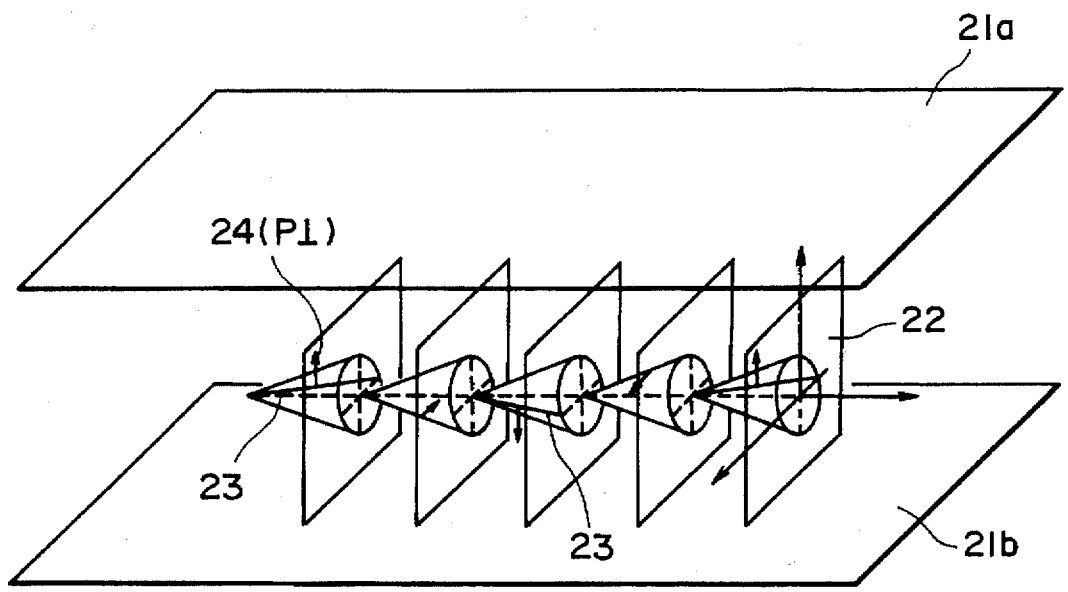
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
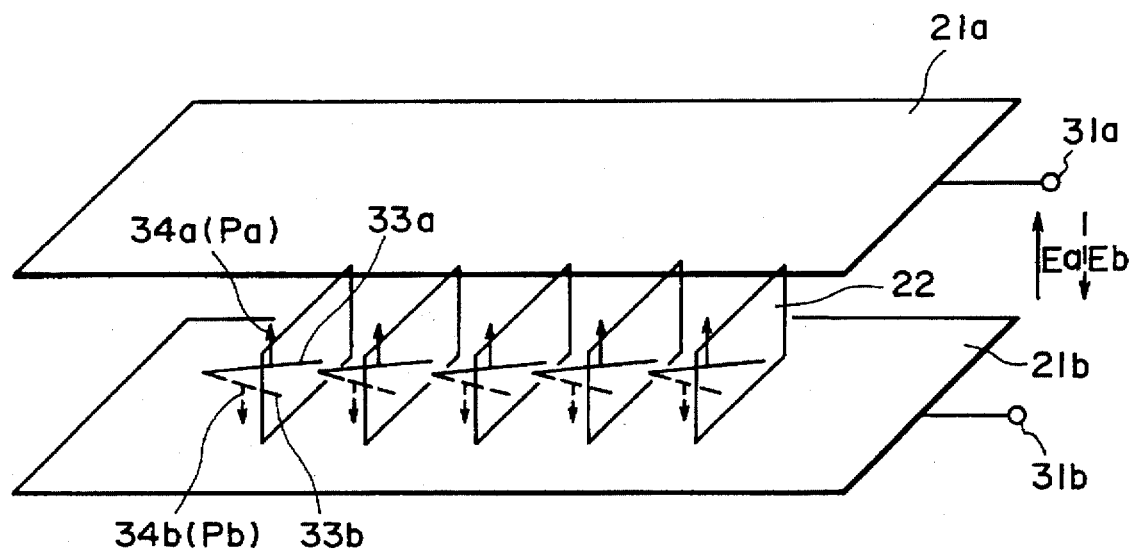

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
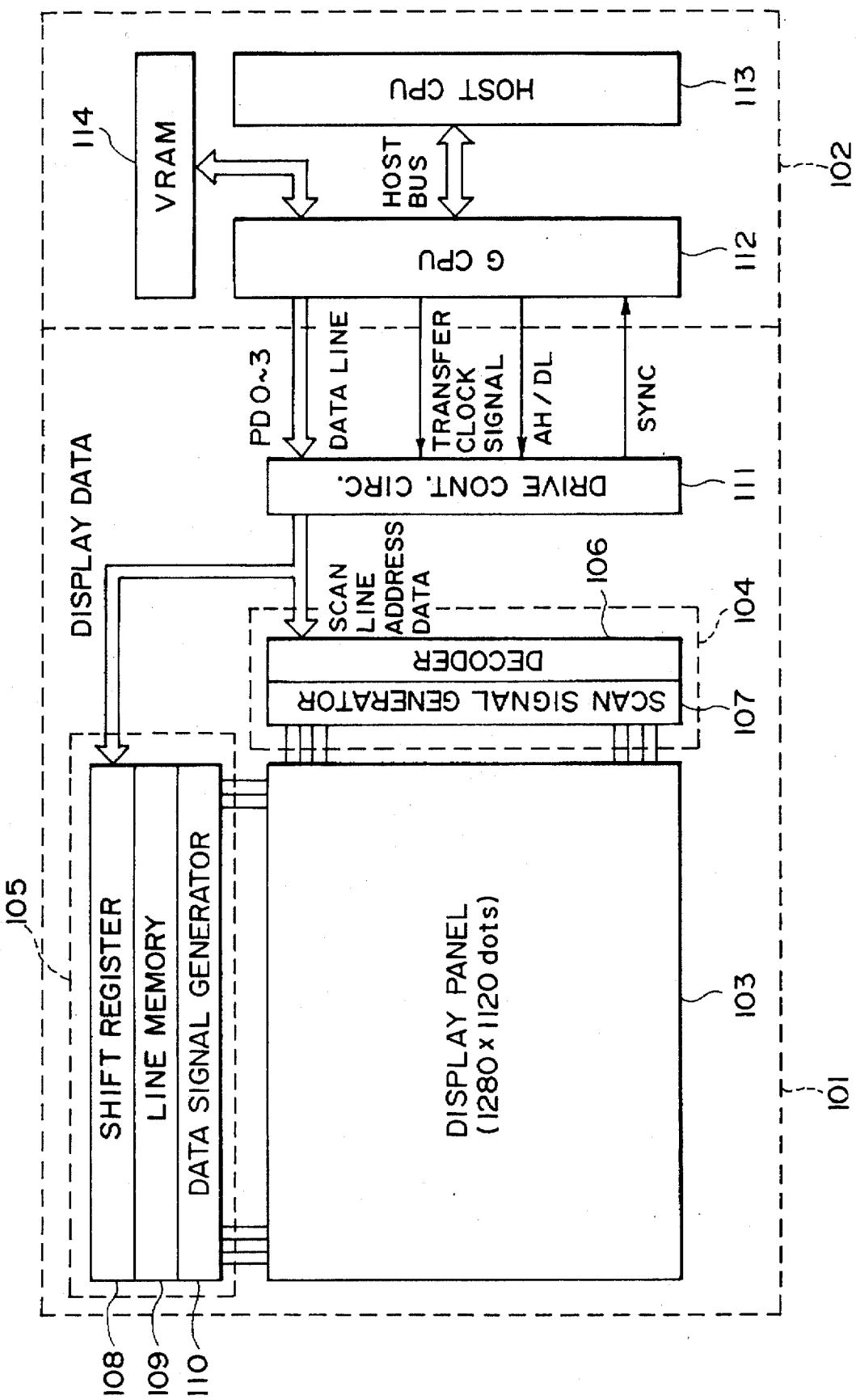
FIG. 4 is a block diagram showing a display apparatus comprising a liquid crystal device utilizing ferroelectricity of a liquid crystal composition and a graphic controller.
Figure 5:
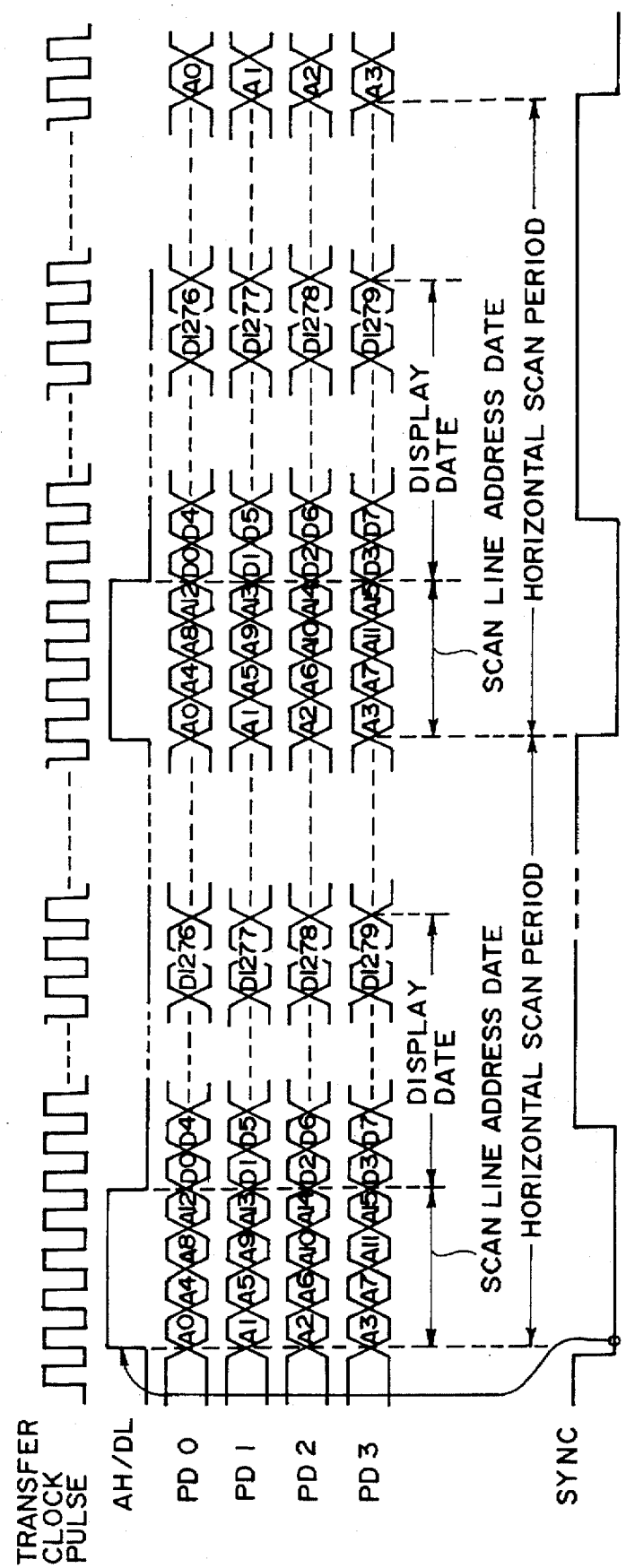
FIG. 5 is a time chart of image data communication showing time correlation between signal transfer and driving with respect to a liquid crystal display apparatus and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically with reference to examples. It is however to be understood that the present invention is not restricted to these examples.

EXAMPLE 1

Optically active 2-[4-(1-trifluoromethylheptyloxymethyl)phenyl]-5-decylpyrimidine (Example Compound No. 19) was synthesized through the following steps i)–iii).

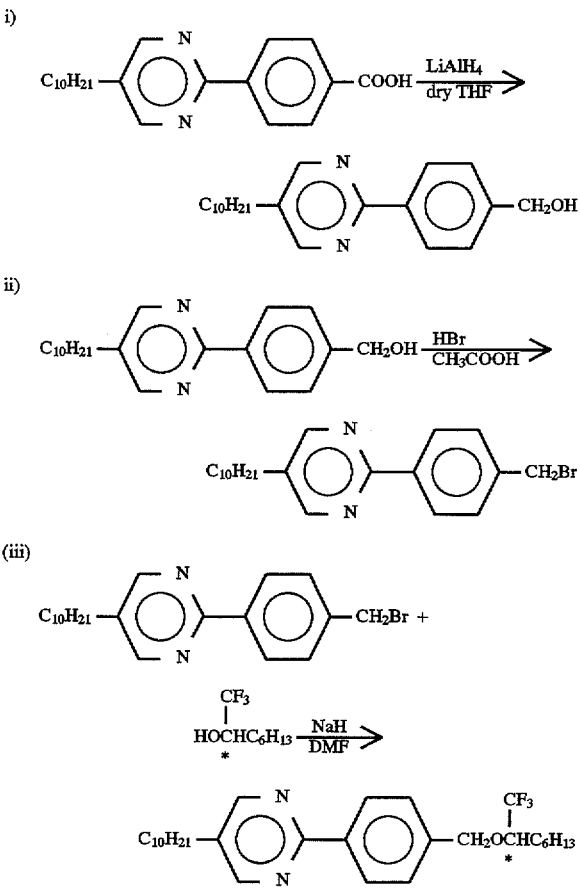

Step i) Production of 2-[4-(hydroxymethyl)phenyl]-5-decylpyrimidine

To a suspension of 49 ml of dry tetrahydrofuran (THF) and 2.36 g of lithium aluminum hydride, a mixture liquid of 20 g (58.8 mM) of 4-(5-decyl-2-pyrimidinyl)benzoic acid and 200 ml of dry THF was added dropwise under cooling with ice, followed by stirring overnight at room temperature. After the reaction, 6M-hydrochloric acid was added to the reaction mixture, followed by extraction with THF and drying with anhydrous sodium sulfate. The solvent of the resultant mixture was distilled off to obtain a crude crystal. The crude crystal was purified by silica gel column chromatography (eluent: chloroform) and recrystallized from ethanol to obtain 8.3 g (25.5 mM) of an objective product (Yield: 43%).

Step ii) Production of 2-[4-(bromomethyl)phenyl]-5-decylpyrimidine

To 4.0 g (12.5 mM) of 2-[4-(hydromethyl)phenyl]-5-decylpyrimidine, 23.0 g of a solution of hydrogen bromide in acetic acid (30% ) was added, followed by stirring for 1 hour at 50° C. After the reaction, cold water was added to the reaction mixture, followed by extraction with THF and drying with anhydrous sodium sulfate. The solvent of the resultant mixture was distilled off to obtain a crude crystal. The crude crystal was purified by silica gel column chromatography (eluent: toluene) to obtain 4.0 g (10.3 mM) of an objective product (Yield: 83%).

Step iii) Production of optically active 2-[4-(1-trifluoromethylheptyloxymethyl)phenyl]-5-decylpyrimidine To a suspension of 1 ml of N,N-dimethylformamide (DMF) and 0.07 g (1.8 mM) of sodium hydride, a mixture liquid of 0.31 g (1.7 mM) of (R)-1,1,1-trifluoro-2-octanol (optical purity: 93%), 0.6 g (1.5 mM) of 2-[4-(bromomethyl)phenyl]-5-decylpyrimidine and 2 ml of DMF was added dropwise, followed by stirring for 5 hours at room temperature. After the reaction, a saturated saline solution was added to the reaction mixture, followed by extraction with ethyl acetate, drying with anhydrous sodium sulfate and distilling-off of the solvent to obtain a crude crystal. The crude crystal was purified by silica gel column chromatography (eluent: toluene) and recrystallized from a mixture solvent (ethyl acetate/methanol) to obtain 0.44 g (0.9 mM) of an objective product (Yield: 60%).

Phase transition temperature (°C.)

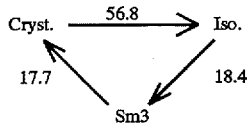

Herein, the respective symbols denote the following phase; Iso.: isotropic phase; Sm3: smectic phase (unidentified); and Cryst.: crystal.

EXAMPLE 2

Optically active 2-[4-(1-monofluoromethylheptyloxymethyl)phenyl]-5-decylpyrimidine (Example Compound No. 18) was synthesized through the following reaction scheme.

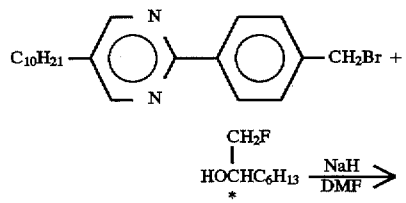

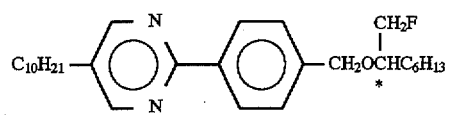

To a suspension of 1 ml of N,N-dimethylformamide (DMF) and 0.07 g (1.8 mM) of sodium hydride, a mixture liquid of 0.25 g (1.7 mM) of (R)-1-fluoro-2-octanol, 0.6 g (1.5 mM) of 2-[4-(bromomethyl)phenyl]-5-decylpyrimidine and 2 ml of DMF was added dropwise, followed by stirring for 5 hours at room temperature. After the reaction, a saturated saline solution was added to the reaction mixture, followed by extraction with ethyl acetate, drying with anhydrous sodium sulfate and distilling-off of the solvent to obtain a crude crystal. The crude crystal was purified by silica gel column chromatography (eluent: toluene) and recrystallized from a mixture solvent (ethyl acetate/methanol) to obtain 0.38 g (0.8 mM) of an objective product (Yield: 56%).

Phase transition temperature (°C.)

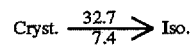

EXAMPLE 3

Optically active 2-[4-(1-methylheptyloxymethyl)phenyl]-5-decylpyrimidine (Example Compound No. 20) was synthesized through the following reaction scheme.

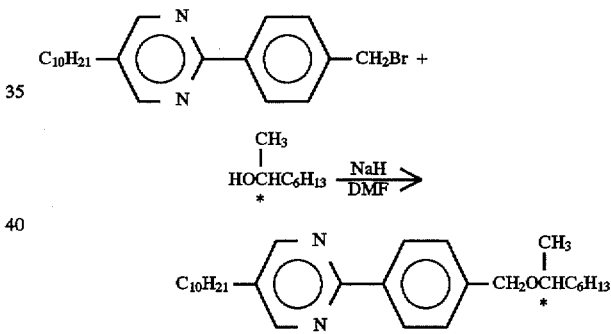

To a suspension of 1 ml of N,N-dimethylformamide (DMF) and 0.07 g (1.8 mM) of sodium hydride, a mixture liquid of 0.22 g (1.7 mM) of (R)-2-octanol, 0.6 g (1.5 mM) of 2-[4-(bromomethyl)phenyl]-5-decylpyrimidine and 2 ml of DMF was added dropwise, followed by stirring for 6 hours at room temperature. After the reaction, a saturated saline solution was added to the reaction mixture, followed by extraction with ethyl acetate, drying with anhydrous sodium sulfate and distilling-off of the solvent to obtain a crude crystal. The crude crystal was purified by silica gel column chromatography (eluent: toluene) and recrystallized from a mixture solvent (ethyl acetate/methanol) to obtain 0.34 g (0.77 mM) of an objective product (Yield: 51%).

Phase transition temperature (°C.)

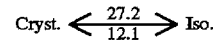

EXAMPLE 4

Optically active 2-[4-(1-methylpropyloxymethyl)phenyl]-5-decylpyrimidine (Example Compound No. 21) was synthesized through the following reaction scheme.

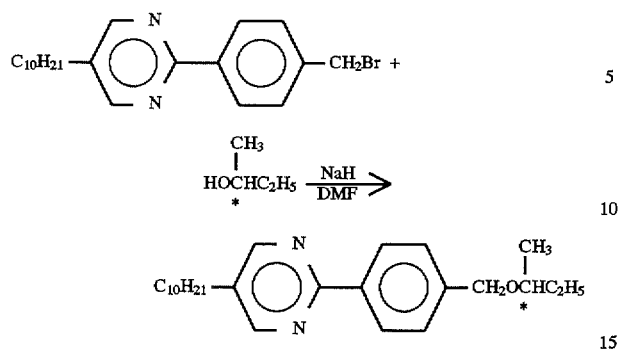

To a suspension of 1 ml of N,N-dimethylformamide (DMF) and 0.07 g (1.8 mM) of sodium hydride, a mixture liquid of 0.11 g (1.5 mM) of (S)-2-butanol, 0.51 g (1.3 mM) of 2-[4-(bromomethyl)phenyl]-5-decylpyrimidine and 2 ml of DMF was added dropwise, followed by stirring for 6 hours at room temperature. After the reaction, a saturated saline solution was added to the reaction mixture, followed by extraction with ethyl acetate, drying with anhydrous sodium sulfate and distilling-off of the solvent to obtain a crude crystal. The crude crystal was purified by silica gel column chromatography (eluent: toluene) and recrystallized from a mixture solvent (ethyl acetate/methanol) to obtain 0.27 g (0.7 mM) of an objective product (Yield: 54%).

Phase transition temperature (°C.)

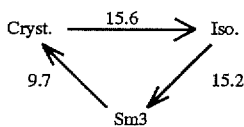

EXAMPLE 5

(±)-2-[4-(1-trifluoromethylheptyloxymethyl)phenyl]-5-decylpyrimidine (Example Compound No. 99) was synthesized in the same manner as in step iii) of Example 1 through the following reaction scheme (Yield: 62%).

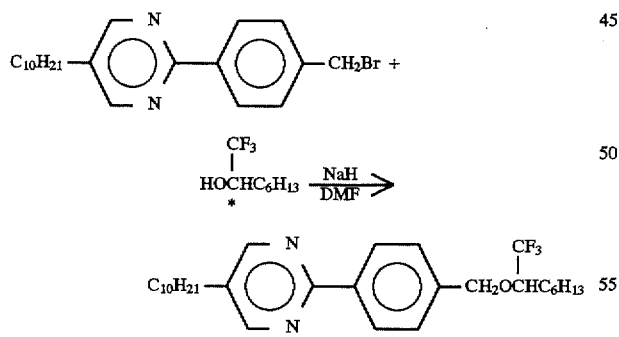

Phase transition temperature (°C.)

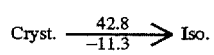

EXAMPLE 6

(±)-2-[4-(1-methylheptyloxymethyl)phenyl]-5-decylpyrimidine (Example Compound No. 100) was synthesized in the same manner as in Example 3 through the following reaction scheme (Yield: 52%).

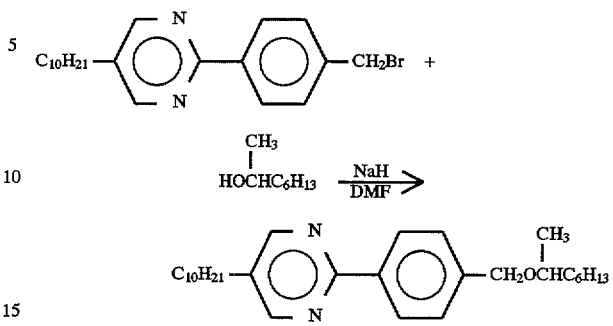

Phase transition temperature (°C.)

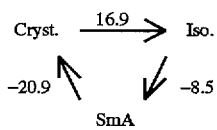

SmA: Smectic A phase

EXAMPLE 7

Optically active ethyl 2-[4-(4-octyloxyphenyl)benzyloxy]propionate (Example Compound No. 5) was synthesized through the following steps i)–iii).

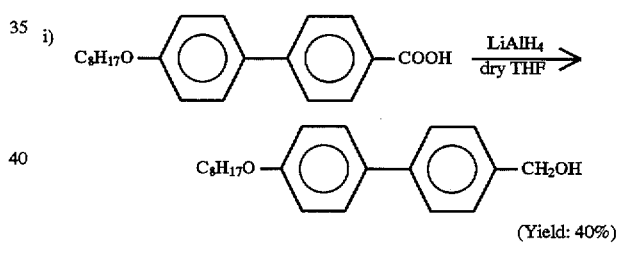

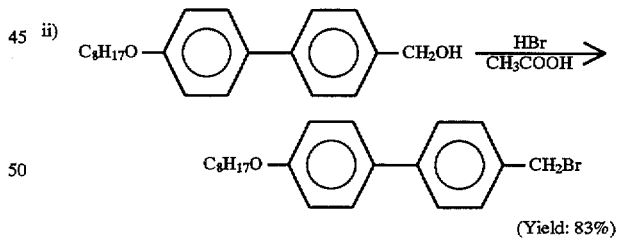

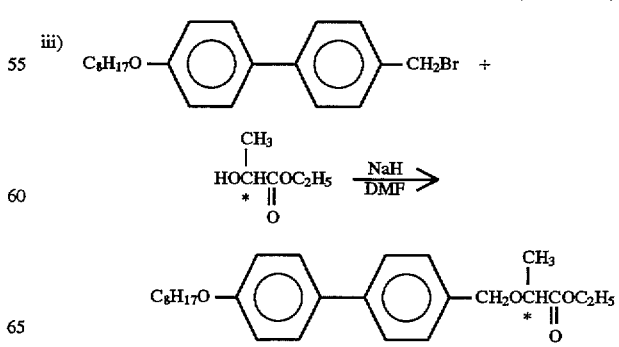

Steps i) and ii)

4-(4-octyloxyphenyl)benzylbromide was prepared in the same manner as in steps i) and ii) of Example 1 with the above-indicated yields.

Step iii) Production of optically active ethyl 2-[4-(4-octyloxyphenyl)benzyloxy]propionate To a suspension of 1 ml of N,N-dimethylformamide (DMF) and 0.06 g (1.5 mM) of sodium hydride, a mixture liquid of 0.19 g (1.6 mM) of L-ethyl lactate, 0.6 g (1.7 mM) of benzyl bromide and 2 ml of DMF was added dropwise, followed by stirring for 6 hours at room temperature. After the reaction, a saturated saline solution was added to the reaction mixture, followed by extraction with ethyl acetate, drying with anhydrous sodium sulfate and distilling-off of the solvent to obtain a crude crystal. The crude crystal was purified by silica gel column chromatography (eluent: toluene) and recrystallized from a mixture solvent (ethyl acetate/methanol) to obtain 0.22 g (0.5 mM) of an objective product (Yield: 36%).

Phase transition temperature (°C.)

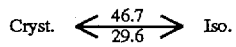

EXAMPLE 8

Optically active 2-[4-(1-methylheptyloxymethyl)phenyl]-5-(4-heptylcyclohexyl)pyrimidine (Example Compound No. 73) was synthesized in the same manner as in Example 1 through the following steps i)–iii).

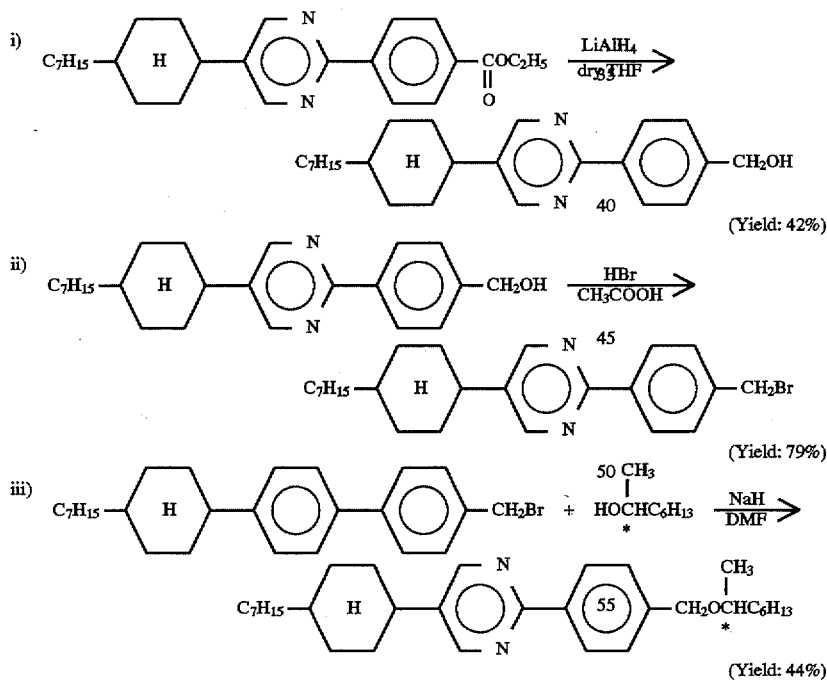

51

Phase transition temperature (°C.)

Cryst. $\xleftrightarrow[-18.4]{36.5}$ SmA $\xleftrightarrow[96.9]{98.4}$ Iso.

EXAMPLE 9

Optically active 2-[4-(1-trifluoromethylheptyloxymethyl) phenyl]-5-(4-butylphenylpyrimidine (Example Compound No. 38) was synthesized in the same manner as in Example 1 through the following steps i)–iii).

52

Phase transition temperature (°C.)

Cryst. $\xleftrightarrow{105}$ Iso.

EXAMPLE 10

A liquid crystal composition A was prepared by mixing the following compounds including a mesomorphic compound (Example Compound No. 19) prepared in Example 1 in respectively indicated proportions.

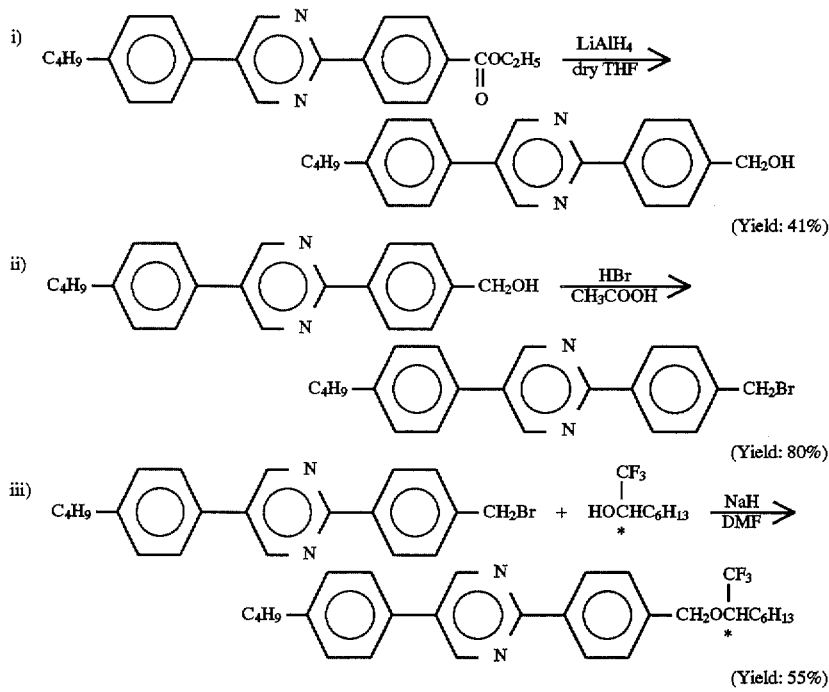

| Ex. Comp. No. | Structural formula | wt. % |
|---|---|---|
|  | $C_8H_{17}O$—⟨⟩—$CO$—$O$—⟨⟩—$OCH_2\overset{*}{C}HC_2H_5$ with $CH_3$ | 76.0 |
|  | $C_8H_{17}O$—⟨⟩—$OC$—$O$—⟨⟩—⟨⟩—$CH_2\overset{*}{C}HC_2H_5$ with $CH_3$ | 19.0 |
| 19 | $C_{10}H_{21}$—⟨N⟩—⟨⟩—$CH_2O\overset{*}{C}HC_6H_{13}$ with $CF_3$ | 5.0 |

Separately, a liquid crystal composition B was prepared by mixing the following compounds including no mesomorphic compound of the present invention in respectively indicated proportions.

| Structural formula | |
|---|---|
| $C_8H_{17}O-\bigcirc-\underset{O}{\underset{\|}{CO}}-\bigcirc-OCH_2\overset{*}{C}HC_2H_5$ with $CH_3$ branch | 80.0 wt. % |
| $C_8H_{17}O-\bigcirc-\underset{O}{\underset{\|}{OC}}-\bigcirc-\bigcirc-CH_2\overset{*}{C}HC_2H_5$ with $CH_3$ branch | 20.0 wt. % |

The above-prepared liquid crystal compositions A and B showed the following phase transition series, respectively.

Phase transition temperature (°C.)

<Composition A>

Cryst. ⇌23⇌ SmC* ⇌46⇌ SmA ⇌62⇌ Ch. ⇌69⇌ Iso.

<Composition B>

Cryst. ⇌20⇌ SmC* ⇌53⇌ SmA ⇌65⇌ Ch. ⇌76⇌ Iso.

SmC*: chiral smectic C phase, and
Ch.: cholesteric phase.

EXAMPLE 11

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, each of the liquid crystal compositions A and B was heated into an isotropic liquid, and injected into the above prepared cell under vacuum and, after sealing, was gradually cooled at a rate of 20° C./hour to 25° C. to prepare a ferroelectric liquid crystal device.

Each of the ferroelectric liquid crystal devices was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

[<Ps ($nC/cm^2$)>]

| Composition | 25° C. | 35° C. | 40° C. |
|---|---|---|---|
| A | 9.7 | 6.0 | 2.0 |
| B | 2.5 | 1.9 | 1.2 |
| <Response time (μsec)> | | | |
| A | 660 | 296 | 82 |
| B | 1280 | 690 | 550 |

As is understood from the above results, the liquid crystal composition A containing the mesomorphic compound (Example Compound No. 19) according to the present invention showed a larger spontaneous polarization and a smaller response time (i.e., faster response speed) compared with those of the liquid crystal composition B containing no mesomorphic compound of the present invention.

EXAMPLE 12

A liquid crystal composition C was prepared by mixing the following compounds in respectively indicated proportions.

| Structural formula | wt. parts |
|---|---|
| $C_6H_{13}O-\bigcirc-\underset{N}{\overset{N}{\bigcirc}}-C_8H_{17}$ | 48.57 |
| | 12.14 |

-continued

| Structural formula | wt. parts |
|---|---|
| C₃H₇—〈H〉—CO—O—〈○〉—〈N○N〉—C₁₁H₂₃ | 3.75 |
| C₄H₉—〈H〉—CO—O—〈○〉—〈N○N〉—C₁₁H₂₃ | 3.75 |
| C₅H₁₁—〈H〉—CO—O—〈○〉—〈N○N〉—C₁₁H₂₃ | 7.50 |

The liquid crystal composition C showed the following phase transition series.

Phase transition temperature (°C.)

Cryst. $\xrightarrow{10.3}$ SmC $\xrightarrow{57.1}$ SmA $\xrightarrow{62.8}$ N $\xrightarrow{78.2}$ Iso.

N: nematic phase, and
SmC: smectic C phase.

The liquid crystal composition C was further mixed with the following Example Compound No. 19 prepared in Example 1 in the proportions indicated below to provide a liquid crystal composition D.

| Ex. Comp. No. | Structural formula | wt. parts |
|---|---|---|
| 19 | C₁₀H₂₁—〈N○N〉—〈○〉—CH₂OCHC₆H₁₃ with CF₃ | 5 |
| | Composition C | 95 |

The liquid crystal composition D showed the following phase transition series.

Phase transition temperature (°C.)

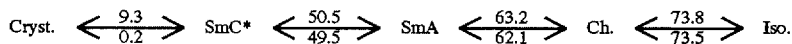

Cryst. $\underset{0.2}{\overset{9.3}{\rightleftarrows}}$ SmC* $\underset{49.5}{\overset{50.5}{\rightleftarrows}}$ SmA $\underset{62.1}{\overset{63.2}{\rightleftarrows}}$ Ch. $\underset{73.5}{\overset{73.8}{\rightleftarrows}}$ Iso.

A ferroelectric liquid crystal device was prepared in the same manner as in Example 11 except for using the composition D. The ferroelectric liquid crystal device was subjected to measurement of the magnitude of spontaneous polarization Ps and response time in the same manner as in Example 11, whereby the following results were obtained.

|  | 30° C. | 40° C. | 45° C. |
| --- | --- | --- | --- |
| Response time (μsec) | 124 | 78 | 40 |
| Ps (nC/cm$^2$) | 4.2 | 2.8 | 1.3 |

EXAMPLE 13

A liquid crystal composition E was prepared by mixing the following Example Compound No. 18 prepared in Example 2 in the indicated proportions with the liquid crystal composition C prepared in Example 12.

| Ex. Comp. No. | Structural formula | wt. parts |
| --- | --- | --- |
| 18 |  | 5 |
| Composition C |  | 95 |

The liquid crystal composition E showed the following phase transition series.

Phase transition temperature (°C.).

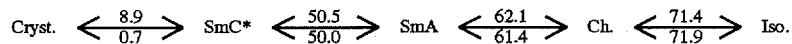

A ferroelectric liquid crystal device was prepared in the same manner as in Example 11 except for using the composition E. The ferroelectric liquid crystal device was subjected to measurement of the magnitude of spontaneous polarization Ps and response time in the same manner as in Example 11, whereby the following results were obtained.

|  | 30° C. | 40° C. | 45° C. |
| --- | --- | --- | --- |
| Response time (μsec) | 310 | 256 | 200 |
| Ps (nC/cm$^2$) | 1.5 | 1.2 | 1.1 |

EXAMPLE 14

A liquid crystal composition F was prepared by mixing the following compounds in the respectively indicated proportions.

| Structural Formula | wt. parts |
| --- | --- |
| C$_6$H$_{13}$O—⟨phenyl⟩—⟨pyrimidine (N,N)⟩—C$_8$H$_{17}$ | 46.14 |
| C$_9$H$_{19}$O—⟨phenyl⟩—⟨pyrimidine (N,N)⟩—C$_8$H$_{17}$ | 23.07 |
| C$_8$H$_{17}$O—⟨phenyl⟩—⟨pyrimidine (N,N)⟩—C$_{10}$H$_{21}$ | 11.54 |

| Structural Formula | wt. parts |
| --- | --- |
| C$_3$H$_7$—⟨cyclohexyl(H)⟩—CO-O—⟨phenyl⟩—⟨pyrimidine (N,N)⟩—C$_{11}$H$_{23}$ | 3.56 |
| C$_4$H$_9$—⟨cyclohexyl(H)⟩—CO-O—⟨phenyl⟩—⟨pyrimidine (N,N)⟩—C$_{11}$H$_{23}$ | 3.56 |
| C$_5$H$_{11}$—⟨cyclohexyl(H)⟩—CO-O—⟨phenyl⟩—⟨pyrimidine (N,N)⟩—C$_{11}$H$_{23}$ | 7.13 |
| C$_{12}$H$_{25}$—⟨pyrimidine (N,N)⟩—⟨phenyl⟩—OCH$_2$C*HC$_6$H$_{13}$ (F) | 2.50 |
| C$_{10}$H$_{21}$—⟨pyrimidine (N,N)⟩—⟨phenyl⟩—OCH$_2$C*HC$_6$H$_{13}$ (F) | 2.50 |

The liquid crystal composition F showed the following phase transition series.

Phase transition temperature (°C.)

$$\text{Cryst.} \xrightarrow{10.0} \text{SmC*} \xrightarrow{56.1} \text{SmA} \xrightarrow{65.0} \text{Ch.} \xrightarrow{77.2} \text{Iso.}$$

A liquid crystal composition H was prepared by mixing the following Example Compound No. 21 prepared in Example 4 in the indicated proportions with the above-prepared liquid crystal composition F.

| Ex. Comp. No. | Structural formula | wt. parts |
| --- | --- | --- |
| 21 | $C_{10}H_{21}-\langle N{=}N \rangle-\langle \rangle-CH_2OCHC_2H_5$ with $CH_3$ branch (*) | 5 |
| | Composition F | 95 |

The liquid crystal composition H showed the following phase transition series.

Phase transition temperature (°C.)

$$\text{Cryst.} \underset{0.9}{\overset{8.7}{\rightleftarrows}} \text{SmC*} \underset{50.3}{\overset{51.4}{\rightleftarrows}} \text{SmA} \underset{62.9}{\overset{63.7}{\rightleftarrows}} \text{Ch.} \underset{73.1}{\overset{73.1}{\rightleftarrows}} \text{Iso.}$$

A ferroelectric liquid crystal device was prepared in the same manner as in Example 11 except for using the composition H. The ferroelectric liquid crystal device was subjected to measurement of the magnitude of spontaneous polarization Ps and response time in the same manner as in Example 11, whereby the following results were obtained.

|  | 30° C. | 40° C. | 45° C. |
| --- | --- | --- | --- |
| Response time (μsec) | 176 | 127 | 97 |
| Ps (nC/cm$^2$) | 3.0 | 2.1 | 1.7 |

Comparative Example 1

A ferroelectric liquid crystal device was prepared in the same manner as in Example 11 except that the liquid crystal composition F prepared in Example 14 was injected into a cell. The ferroelectric liquid crystal device was subjected to measurement of the magnitude of spontaneous polarization Ps and response time in the same manner as in Example 11, whereby the following results were obtained.

|  | 30° C. | 40° C. |
| --- | --- | --- |
| Response time (μsec) | 237 | 167 |
| Ps (nC/cm$^2$) | 2.8 | 2.1 |

EXAMPLE 15

A liquid crystal composition I was prepared by mixing the following Example Compound No. 99 prepared in Example 5 in the indicated proportions with the liquid crystal composition F prepared in Example 14.

| Ex. Comp. No. | Structural formula | wt. parts |
| --- | --- | --- |
| 99 | $C_{10}H_{21}-\langle N{=}N \rangle-\langle \rangle-CH_2OCHC_6H_{13}$ with $CF_3$ branch | 5 |
| | Composition F | 95 |

The liquid crystal composition I showed the following phase transition series.

Phase transition temperature (°C.)

$$\text{Cryst.} \underset{0.9}{\overset{9.1}{\rightleftarrows}} \text{SmC*} \underset{51.1}{\overset{52.0}{\rightleftarrows}} \text{SmA} \underset{63.2}{\overset{64.1}{\rightleftarrows}} \text{Ch.} \underset{72.8}{\overset{72.5}{\rightleftarrows}} \text{Iso.}$$

A ferroelectric liquid crystal device was prepared in the same manner as in Example 11 except for using the composition I. The ferroelectric liquid crystal device was subjected to measurement of the magnitude of spontaneous polarization Ps and response time in the same manner as in Example 11, whereby the following results were obtained.

|  | 30° C. | 40° C. | 45° C. |
| --- | --- | --- | --- |
| Response time (μsec) | 190 | 128 | 95 |
| Ps (nC/cm$^2$) | 2.4 | 1.8 | 1.1 |

EXAMPLE 16

A liquid crystal composition J was prepared by mixing the following Example Compound No. 100 prepared in Example 6 in the indicated proportions with the liquid crystal composition F prepared in Example 14.

| Ex. Comp. No. | Structural formula | wt. parts |
|---|---|---|
| 100 |  | 5 |
| | Composition F | 95 |

The liquid crystal composition J showed the following phase transition series.

Phase transition temperature (°C.)

$$\text{Cryst.} \xrightarrow{9.3}_{0.9} \text{SmC*} \xrightarrow{52.5}_{51.5} \text{SmA} \xrightarrow{63.7}_{63.1} \text{Ch.} \xrightarrow{72.5}_{73.1} \text{Iso.}$$

A ferroelectric liquid crystal device was prepared in the same manner as in Example 11 except for using the composition J. The ferroelectric liquid crystal device was subjected to measurement of the magnitude of spontaneous polarization Ps and response time in the same manner as in Example 11, whereby the following results were obtained.

|  | 30° C. | 40° C. | 45° C. |
|---|---|---|---|
| Response time (μsec) | 194 | 137 | 106 |
| Ps (nC/cm$^2$) | 2.5 | 1.9 | 1.3 |

EXAMPLE 17

A liquid crystal composition K was prepared by mixing the following Example Compound No. 73 prepared in Example 8 in the indicated proportions with the liquid crystal composition F prepared in Example 14.

| Ex. Comp. No. | Structural formula | wt. parts |
|---|---|---|
| 73 | 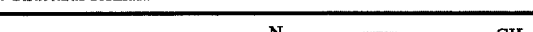 | 5 |
| | Composition F | 95 |

The liquid crystal composition K showed the following phase transition series.

Phase transition temperature (°C.)

$$\text{Cryst.} \xrightarrow{9.4}_{0.9} \text{SmC*} \xrightarrow{45.5}_{44.9} \text{SmA} \xrightarrow{69.9}_{69.7} \text{Ch.} \xrightarrow{78}_{77.5} \text{Iso.}$$

A ferroelectric liquid crystal device was prepared in the same manner as in Example 11 except for using the composition K. The ferroelectric liquid crystal device was subjected to measurement of the magnitude of spontaneous polarization Ps and response time in the same manner as in Example 11, whereby the following results were obtained.

|  | 30° C. | 40° C. |
|---|---|---|
| Response time (μsec) | 142 | 60 |
| Ps (nC/cm$^2$) | 2.0 | 1.1 |

EXAMPLE 18

Two glass plates were provided respectively coated with an ITO film to form a transparent electrode, which was further coated with a solution of polyimide resin precursor (SP-510, available from Toray K.K.) by a spinner coater to obtain a polyimide film. Each coating film was subjected to rubbing. The thus treated two glass plates were applied each other so that their rubbed directions were at right angles to each other to form a blank cell with a cell gap of 8 microns.

A nematic liquid crystal composition (Lixon GR-63 (biphenyl liquid crystal mixture), available from Chisso K.K.) was injected into the above-prepared cell to prepare a TN-type liquid crystal device (or cell).

When the TN-type liquid crystal device was subjected to observation with a polarizing microscope, occurrence of a reverse domain or twist discrimination (i.e., a striped pattern) was recognized.

On the other hand, a TN-type liquid crystal device was prepared by mixing 1 wt. part of a mesomorphic compound (Ex. Comp. No. 19) prepared in Example 1 according to the present invention with 99 wt. parts of the above-mentioned nematic liquid crystal composition (Lixon GR-63), and injected into a blank cell to provide a TN-type liquid crystal device in the same manner as described above.

When the device was subjected to observation with a polarizing microscope, uniform nematic phase free from reverse domain was observed.

As described hereinabove, according to the present invention, there is provided a mesomorphic compound effective for providing a liquid crystal composition and a liquid crystal device using the composition which can provide improved response speed and also effectively for suppressing occurrence of reverse domain. The present invention further provides a display apparatus and a display method which employ such a device as a display unit, whereby good display characteristics can be obtained in combination with a light source, a drive circuit, etc.

What is claimed is:

1. A mesomorphic compound represented by the following formula (I):

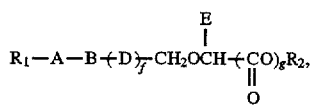

wherein $R_1$ denotes a linear or branched alkyl group having 1–18 carbon atoms capable of including one or non-neighboring two or more methylene groups which can be replaced with at least one species of

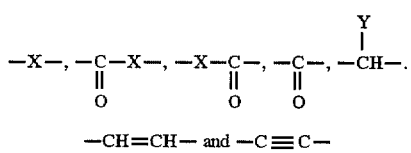

wherein X denotes O or S and Y denotes halogen; $R_2$ denotes a linear or branched alkyl group having 1–18 carbon atoms; A, B, and D independently denote

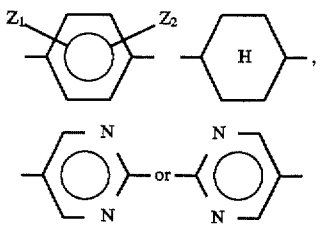

wherein $Z_1$ and $Z_2$ independently denote hydrogen, halogen, —$CH_3$, —CN or —$CF_3$; E denotes —$CH_3$, —$CH_2F$ or —$CF_3$; and f and g independently denote 0 or 1, with the provisos that (i) E is —$CH_3$ or —$CH_2F$ when —A—B— is

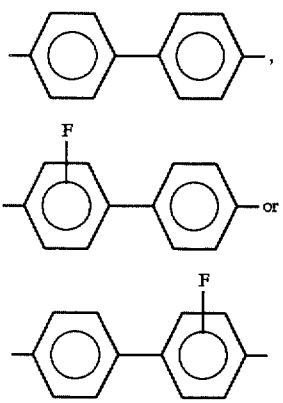

and f and g are zero, and (ii) that g is 0 when E is —$CH_3$.

2. A mesomorphic compound according to claim 1, wherein $R_1$ denotes a linear or branched alkyl group having 1–18 carbon atoms including at least one methylene group replaced with

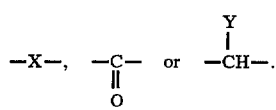

3. A mesomorphic compound according to claim 1, wherein $R_1$ denotes any one of the following groups (i) to (iv):

(i) —G—$C_aH_{2a+1}$-n wherein G denotes a single bond,

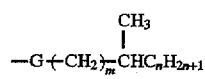

and a is an integer of 1–18;

(ii)

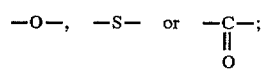

wherein G denotes a single bond

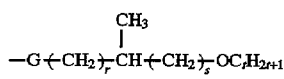

m is an integer of 0–7 and n is an integer of 1–9;

(iii)

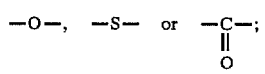

wherein G denotes a single bond,

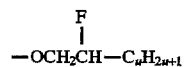

r is an integer of 0–7; s is 0 or 1 and t is an integer of 1–14; and (iv)

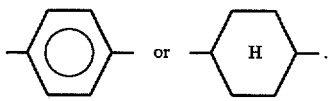

wherein u is an integer of 1–16.

4. A mesomorphic compound according to claim 1, wherein $R_2$ denotes any of the following groups (i) or (ii):
   (i) an n-alkyl group having 4–8 carbon atoms with the proviso that E is —$CH_2F$; and
   (ii) an n-alkyl group having 2–12 carbon atoms with the proviso that E is —$CH_3$ and g is 0.

5. A mesomorphic compound according to claim 1, wherein at least two constituents of A, B and D independently denote

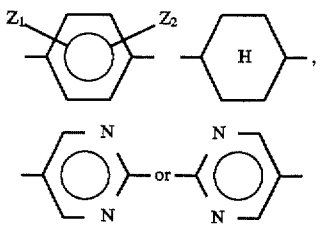

6. A mesomorphic compound according to claim 1, which is an optically active compound.

7. A liquid crystal composition comprising at least two mesomorphic compounds, at least one of which is a mesomorphic compound of the formula (I) according to claim 1.

8. A liquid crystal composition according to claim 7, wherein $R_1$ in the formula (I) denotes a linear or branched alkyl group having 1–18 carbon atoms including at least one methylene group replaced with

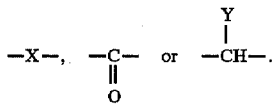

9. A liquid crystal composition according to claim 7, wherein $R_1$ in the formula (I) denotes any one of the following groups (i) to (iv):

(i) —G—$C_aH_{2a+1}$-n wherein G denotes a single bond,

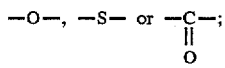

and a is an integer of 1–18;

(ii)

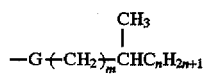

wherein G denotes a single bond

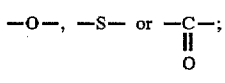

m is an integer of 0–7 and n is an integer of 1–9;

(iii)

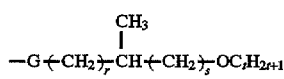

wherein G denotes a single bond,

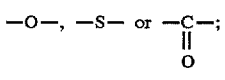

r is an integer of 0–7; s is 0 or 1 and t is an integer of 1–14; and (iv)

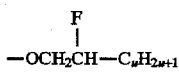

wherein u is an integer of 1–16.

10. A liquid crystal composition according to claim 7, wherein $R_2$ in the formula (I) denotes any one of the following groups (i) to (iii):

(i) an n-alkyl group having 4–8 carbon atoms with the proviso that E is —$CH_2F$;

(ii) an n-alkyl group having 2–12 carbon atoms with the proviso that E is —$CH_3$ and g is 0; and (iii) an n-alkyl group having 1–12 carbon atoms with the proviso that E is —$CH_3$ and g is 1.

11. A liquid crystal composition according to claim 7, wherein at least two constituents of A, B and D in the formula (I) independently denote

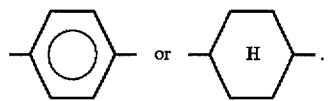

12. A liquid crystal composition according to claim 7, which has a chiral smectic phase.

13. A liquid crystal composition according to claim 7, which comprises 1–80 wt. % of a mesomorphic compound of the formula (I).

14. A liquid crystal composition according to claim 7, which comprises 1–60 wt. % of a mesomorphic compound of the formula (I).

15. A liquid crystal composition according to claim 7, which comprises 1–40 wt. % of a mesomorphic compound of the formula (I).

16. A liquid crystal device, comprising a pair of electrode plates and a liquid crystal composition according to claim 7 disposed between the electrode plates.

17. A liquid crystal device according to claim 16, wherein $R_1$ in the formula (I) denotes a linear or branched alkyl group having 1–18 carbon atoms including at least one methylene group replaced with

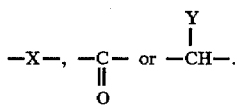

18. A liquid crystal device according to claim 16, wherein $R_1$ in the formula (I) denotes any one of the following groups (i) to (iv):

(i) —G—$C_aH_{2a+1}$-n wherein G denotes a single bond,

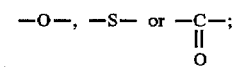

and a is an integer of 1–18;

(ii)

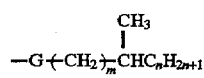

wherein G denotes a single bond

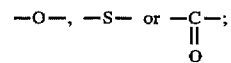

m is an integer of 0–7 and n is an integer of 1–9;

(iii)

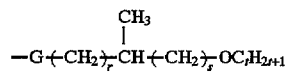

wherein G denotes a single bond,

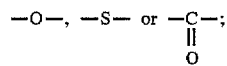

r is an integer of 0–7; s is 0 or 1 and t is an integer of 1–14; and (iv)

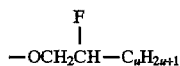

wherein u is an integer of 1–16.

19. A liquid crystal device according to claim 6, wherein $R_2$ in the formula (I) denotes any of the following groups (i) to (ii):

(i) an n-alkyl group having 4–8 carbon atoms with the proviso that E is —$CH_2F$; and (ii) an n-alkyl group having 2–12 carbon atoms with the proviso that E is —$CH_3$ and g is 0.

20. A liquid crystal device according to claim 16, wherein at least two constituents of A, B and D in the formula (I) independently denote

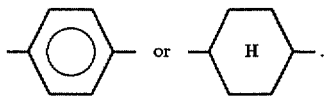

21. A liquid crystal device according to claim 16, wherein the liquid crystal composition has a chiral smectic phase.

22. A liquid crystal device according to claim 16, wherein the liquid crystal composition comprises 1–80 wt. % of a mesomorphic compound of the formula (I).

23. A liquid crystal device according to claim 16, wherein the liquid crystal composition comprises 1–60 wt. % of a mesomorphic compound of the formula (I).

24. A liquid crystal device according to claim 16, wherein the liquid crystal composition comprises 1–40 wt. % of a mesomorphic compound of the formula (I).

25. A liquid crystal device according to claim 16, which further comprises an insulating alignment control layer.

26. A liquid crystal device according to claim 25, wherein the insulating alignment control layer has been subjected to rubbing.

27. A liquid crystal device according to claim 16, wherein the liquid crystal composition is disposed in a thickness suppressing formation of a helical structure of liquid crystal molecules between the electrode plates.

28. A display apparatus comprising a liquid crystal device according to claim 16, and voltage application means for driving the liquid crystal device.

29. A display apparatus according to claim 28, wherein $R_1$ in the formula (I) denotes a linear or branched alkyl group having 1–18 carbon atoms including at least one methylene group replaced with

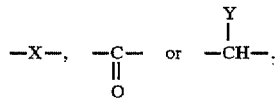

30. A display apparatus according to claim 28, wherein $R_1$ in the formula (I) denotes any one of the following groups (i) to (iv):

(i) —G—$C_aH_{2a+1}$-n wherein G denotes a single bond,

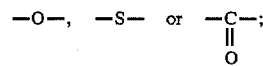

and a is an integer of 1–18;

(ii)

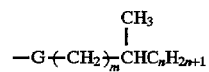

wherein G denotes a single bond

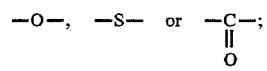

m is an integer of 0–7 and n is an integer of 1–9;

(iii)

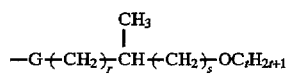

wherein G denotes a single bond,

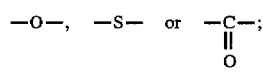

r is an integer of 0–7; s is 0 or 1 and t is an integer of 1–14; and (iv)

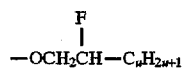

wherein u is an integer of 1–16.

31. A display apparatus according to claim 28, wherein $R_2$ in the formula (I) denotes any of the following groups (i) or (ii):

(i) an n-alkyl group having 4–8 carbon atoms with the proviso that E is —$CH_2F$; and (ii) an n-alkyl group having 2–12 carbon atoms with the proviso that E is —$CH_3$ and g is 0.

32. A display apparatus according to claim 28, wherein at least two constituents of A, B and D in the formula (I) independently denote

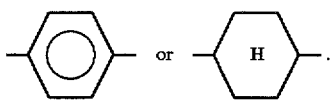

33. A display apparatus according to claim 28, wherein the mesomorphic compound of the formula (I) is an optically active compound.

34. A display apparatus according to claim 28, which further comprises a drive circuit.

35. A display apparatus according to claim 28, which further comprises a light source.

36. A display method, comprising:

providing a liquid crystal composition comprising at least two mesomorphic compound, at least one of which is a mesomorphic compound of the formula (I) according to claim 1; and switching the alignment direction of liquid crystal molecules by applying voltages to the liquid crystal composition to effect display.

37. A display method according to claim 36, wherein $R_1$ in the formula (I) denotes a linear or branched alkyl group having 1–18 carbon atoms including at least one methylene group replaced with

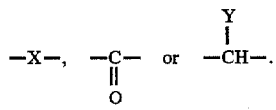

38. A display method according to claim 36, wherein $R_1$ in the formula (I) denotes any one of the following groups (i) to (iv):

(i) —G—$C_aH_{2a+1}$-n wherein G denotes a single bond,

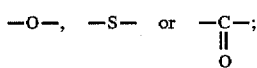

and a is an integer of 1–18;

(ii)

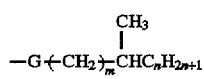

wherein G denotes a single bond

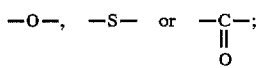

m is an integer of 0–7 and n is an integer of 1–9;

(iii)

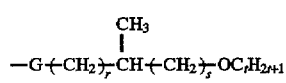

wherein G denotes a single bond,

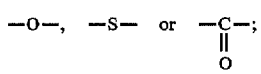

r is an integer of 0–7; s is 0 or 1 and t is an integer of 1–14; and (iv)

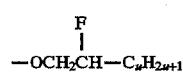

wherein u is an integer of 1–16.

39. A display method according to claim 36, wherein $R_2$ in the formula (I) denotes any of the following groups (i) or (ii):

(i) an n-alkyl group having 4–8 carbon atoms with the proviso that E is —$CH_2F$; and (ii) an n-alkyl group having 2–12 carbon atoms with the proviso that E is —$CH_3$ and g is 0.

40. A display method according to claim 36, wherein at least two constituents of A, B and D in the formula (I) independently denote

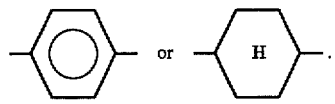

41. A display method according to claim 36, wherein the mesomorphic compound of the formula (I) is an optically active compound.

42. A display method according to claim 36, wherein the liquid crystal composition has a chiral smectic phase.

43. A display method according to claim 36, wherein the liquid crystal composition comprises 1–80 wt. % of a mesomorphic compound of the formula (I).

44. A display method according to claim 36, wherein the liquid crystal composition comprises 1–60 wt. % of a mesomorphic compound of the formula (I).

45. A display method according to claim 36, wherein the liquid crystal composition comprises 1–40 wt. % of a mesomorphic compound of the formula (I).

46. A display method, comprising:

providing a liquid crystal device comprising a pair of electrode plates and a liquid crystal composition disposed therebetween comprising at least two mesomorphic compound, at least one of which is a mesomorphic compound of the formula (I) according to claim 1; and switching the alignment direction of liquid crystal molecules by applying voltages to the liquid crystal composition disposed between the electrode plates to effect display.

47. A display method according to claim 46, wherein $R_1$ in the formula (I) denotes a linear or branched alkyl group having 1–18 carbon atoms including at least one methylene group replaced with

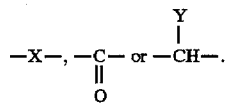

48. A display method according to claim 46, wherein $R_1$ in the formula (I) denotes any one of the following groups (i) to (iv):

(i) —G—$C_aH_{2a+1}$-n wherein G denotes a single bond,

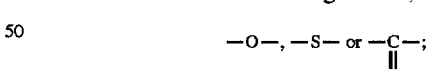

and a is an integer of 1–18;

(ii)

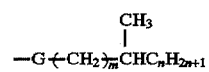

wherein G denotes a single bond

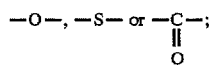

m is an integer of 0–7 and n is an integer of 1–9;

(iii)

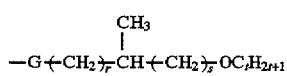

wherein G denotes a single bond,

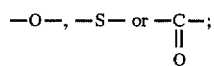

r is an integer of 0–7; s is 0 or 1 and t is an integer of 1–14; and (iv)

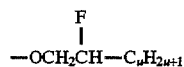

wherein u is an integer of 1–16.

49. A display method according to claim 46, wherein $R_2$ in the formula (I) denotes any of the following groups (i) or (ii):
  (i) an n-alkyl group having 4–8 carbon atoms with the proviso that E is —$CH_2F$; and
  (ii) an n-alkyl group having 2–12 carbon atoms with the proviso that E is —$CH_3$ and g is 0.

50. A display method according to claim 46, wherein at least two constituents of A, B and D in the formula (I) independently denote

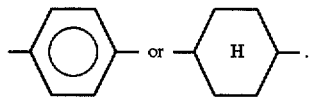

51. A display method according to claim 46, wherein the mesomorphic compound of the formula (I) is an optically active compound.

* * * * *

UNITED STATES PATENT AND TRADEMARK OFFICE
CERTIFICATE OF CORRECTION

PATENT NO. : 5,686,020

DATED : November 11, 1997

INVENTOR(S): HIROYUKI NOHIRA ET AL.

It is certified that error appears in the above-identified patent and that said Letters Patent is hereby corrected as shown below:

COLUMN 1
  Line 12, "composition" should read --composition,--;
  Line 33, "milli-seconds," should read --milliseconds,--.

COLUMN 2
  Line 27, "and" should read --or--;
  Line 30, "electric" should read --electric field--.

COLUMN 3
  Line 4, "that" should read --that a--.

COLUMN 4
  Line 36, "14 18" should read --1-18--.

COLUMN 17
  Form 83, "$\overset{CF_3}{|}$" should read --$\overset{CH_3}{|}$--.

COLUMN 36
  Line 2, "(X)" should be deleted;
  Line 7, insert --(X)-- at right margin.

COLUMN 45
  Line 49, "phase;" should read --phases:-- (1st occur.)

UNITED STATES PATENT AND TRADEMARK OFFICE
CERTIFICATE OF CORRECTION

PATENT NO. : 5,686,020

DATED : November 11, 1997

INVENTOR(S): HIROYUKI NOHIRA ET AL.

It is certified that error appears in the above-identified patent and that said Letters Patent is hereby corrected as shown below:

COLUMN 49
Line 32 i) 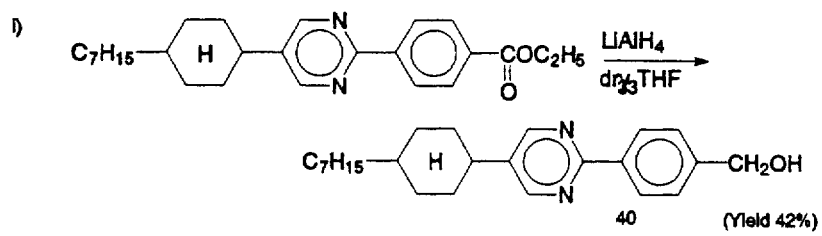

ii) 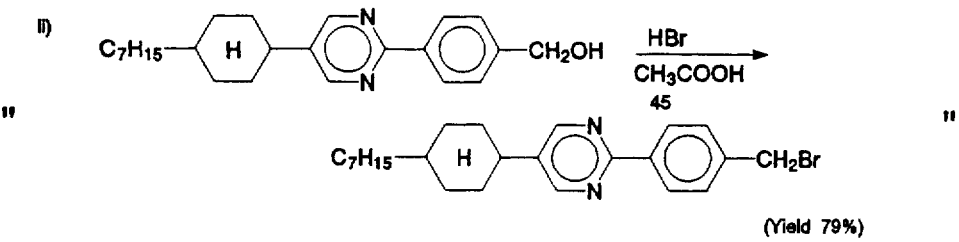

iii) 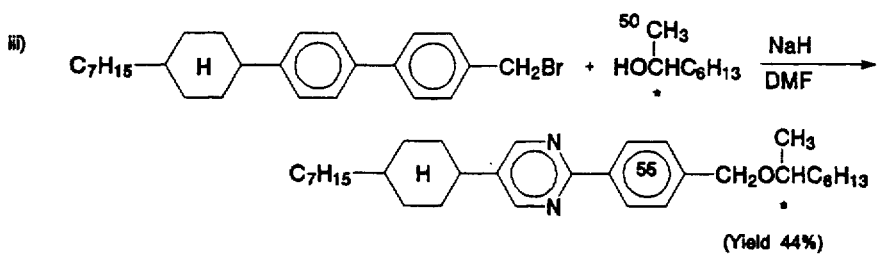

should read (see next page)

UNITED STATES PATENT AND TRADEMARK OFFICE
CERTIFICATE OF CORRECTION

PATENT NO. : 5,686,020

DATED : November 11, 1997

INVENTOR(S): HIROYUKI NOHIRA ET AL.

It is certified that error appears in the above-identified patent and that said Letters Patent is hereby corrected as shown below:

i) 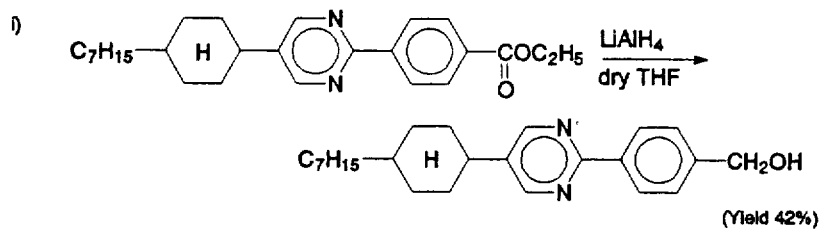

ii) 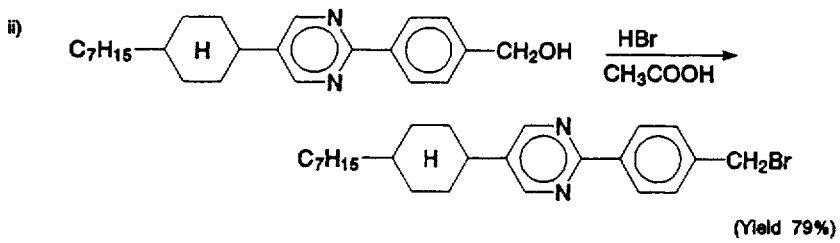

iii) 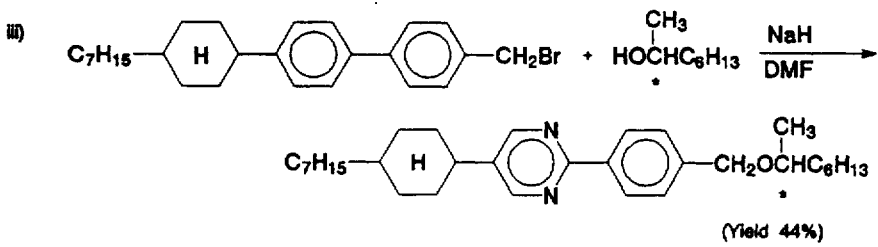

UNITED STATES PATENT AND TRADEMARK OFFICE
CERTIFICATE OF CORRECTION

PATENT NO. : 5,686,020

DATED : November 11, 1997

INVENTOR(S): HIROYUKI NOHIRA ET AL.

It is certified that error appears in the above-identified patent and that said Letters Patent is hereby corrected as shown below:

COLUMN 53
 Line 42, "second" should read --seconds--;
 Line 61, "and." should read --and--.

COLUMN 54
 Line 60,

"              48.57

12.14       "

should read

--      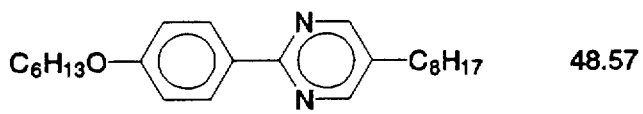       48.57

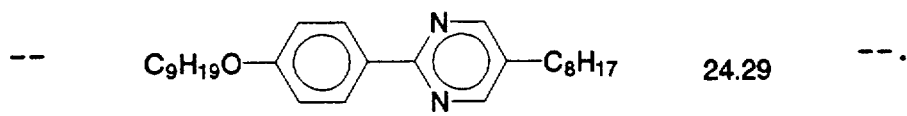       24.29

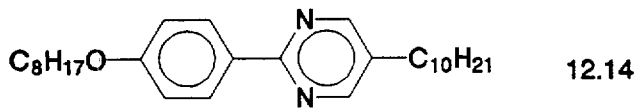       12.14       --.

UNITED STATES PATENT AND TRADEMARK OFFICE
CERTIFICATE OF CORRECTION

PATENT NO. : 5,686,020

DATED : November 11, 1997

INVENTOR(S): HIROYUKI NOHIRA ET AL.

Page 5 of 5

It is certified that error appears in the above-identified patent and that said Letters Patent is hereby corrected as shown below:

COLUMN 62
Line 28, "each" should read --to each--.

COLUMN 63
Line 44, "provisos that (i)" should read --proviso that--;
Line 63, "zero, and (ii) that g is 0 when E is —$CH_3$." should read --zero.--.

COLUMN 65
Line 62, "is" should read --is —$CF_3$ or--.

COLUMN 67
Line 18, "to" should read --or--.

COLUMN 68
Line 67, "compound," should read --compounds,--.

COLUMN 70
Line 28, "compound," should read --compounds,--.

Signed and Sealed this

Twenty-sixth Day of May, 1998

Attest:

BRUCE LEHMAN

*Attesting Officer*    *Commissioner of Patents and Trademarks*